(12) United States Patent
Kawai et al.

(10) Patent No.: US 8,765,814 B2
(45) Date of Patent: Jul. 1, 2014

(54) N-HYDROXYFORMAMIDE DERIVATIVE AND MEDICAMENT CONTAINING SAME

(75) Inventors: Kentaro Kawai, Shiga (JP); Shigeru Miyamoto, Kyoto (JP); Masanao Shimano, Shigo (JP); Makoto Haino, Shizuoka (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/809,027

(22) PCT Filed: Jul. 5, 2011

(86) PCT No.: PCT/JP2011/065317
§ 371 (c)(1),
(2), (4) Date: Jan. 31, 2013

(87) PCT Pub. No.: WO2012/005229
PCT Pub. Date: Jan. 12, 2012

(65) Prior Publication Data
US 2013/0131180 A1    May 23, 2013

(30) Foreign Application Priority Data
Jul. 8, 2010    (JP) .................................. 2010-156025

(51) Int. Cl.
*A01N 41/12*    (2006.01)
*A61K 31/16*    (2006.01)

(52) U.S. Cl.
USPC .......................................... 514/609; 564/99

(58) Field of Classification Search
None
See application file for complete search history.

(56) References Cited

U.S. PATENT DOCUMENTS

| | | | |
|---|---|---|---|
| 6,100,266 A | 8/2000 | Montana et al. | |
| 6,340,691 B1 | 1/2002 | Levin et al. | |
| 6,358,980 B1 | 3/2002 | Levin et al. | |
| 6,734,184 B1 | 5/2004 | Barlaam et al. | |
| 2003/0212056 A1 | 11/2003 | Duan et al. | |
| 2004/0186088 A1 | 9/2004 | Bamdarage et al. | |
| 2004/0214928 A1 | 10/2004 | Aronov et al. | |
| 2004/0232928 A1 | 11/2004 | Boyle et al. | |
| 2004/0242928 A1 | 12/2004 | Shimano et al. | |
| 2005/0227973 A1 | 10/2005 | Brown et al. | |
| 2006/0058350 A1 | 3/2006 | Tsukida et al. | |
| 2006/0063783 A1 | 3/2006 | Burrows et al. | |

FOREIGN PATENT DOCUMENTS

| | | |
|---|---|---|
| CN | 1225623 A | 8/1999 |
| CN | 1289322 A | 3/2001 |
| CN | 1668302 A | 9/2005 |
| EP | 1431285 A1 | 6/2004 |
| JP | 11-511179 | 9/1999 |
| JP | 2002-501943 | 1/2002 |
| JP | 2006-502990 | 1/2006 |
| JP | 2006-515319 | 5/2006 |
| WO | WO 97/43245 | 11/1997 |
| WO | WO 99/06361 | 2/1999 |
| WO | WO 00/44709 | 8/2000 |
| WO | WO 00/44730 | 8/2000 |
| WO | WO 03/022801 | 3/2003 |
| WO | WO 03/051825 | 6/2003 |
| WO | WO 2004/006927 | 1/2004 |
| WO | WO 2004/056766 | 7/2004 |

OTHER PUBLICATIONS

Levine, Bioorganic & Medicinal Chemistry, Letters 13 (2003) 2799-2803.*
Arribas et al, Current Pharmaceutical Design, 2009, 15, 1-17.*
International Search Report for PCT/JP2011/065317, mailed Oct. 4, 2011.
English translation of International Preliminary Report on Patentability in PCT/JP2011/065317 mailed Feb. 21, 2013.
International Preliminary Report on Patentability in PCT/2011/065317 mailed Jan. 17, 2013.
Official Action cited in corresponding Chinese patent application No. 201180033829.6, with English translation (Aug. 1, 2013).
European Search Report dated Mar. 14, 2014, Application No. 11803563.3—1451/2597084 PCT/JP2011065317 (5 pgs).

* cited by examiner

*Primary Examiner* — Wu-Cheng Winston Shen
*Assistant Examiner* — Jean Cornet
(74) *Attorney, Agent, or Firm* — Nixon & Vanderhye P.C.

(57) ABSTRACT

A compound represented by the following general formula (I) which has ADAM17 inhibitory activity, or a salt thereof, or a solvate thereof:

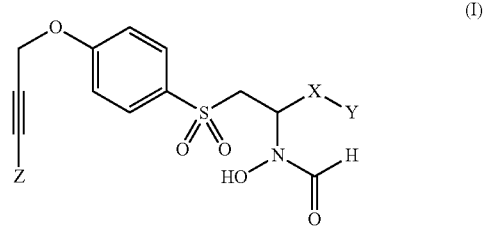

(I)

wherein X represents a phenylene group; Y represents a hydrogen atom, $-(CH_2)_m R^1$ or the like; $R^1$ represents $-NR^5COR^2$, $-NR^5SO_2R^2$ or $-NR^3R^4$; $R^2$ represents a C1-C6 alkyl group, an aryl group, or a C1-C6 alkoxy group; $R^3$ and $R^4$ represent a C1-C6 alkyl group and the like; $R^5$ represents a hydrogen atom or a C1-C6 alkyl group or the like; m indicates an integer of from 0 to 4; and Z represents a hydrogen atom or a C1-C6 alkyl group.

5 Claims, No Drawings

N-HYDROXYFORMAMIDE DERIVATIVE AND MEDICAMENT CONTAINING SAME

This application is the U.S. national phase of International Application No. PCT/JP2011/065317, filed 5 Jul. 2011, which designated the U.S. and claims priority to 2010-156025, filed 8 Jul. 2010, the entire contents of each of which are hereby incorporated by reference.

TECHNICAL FIELD

The present invention relates to a novel N-hydroxyformamide derivative and to a medicament containing the derivative as an active ingredient.

BACKGROUND ART

ADAM (a disintegrin and metalloproteinase) family is a membrane-associated protease having zinc in the catalytic site. ADAM17 cleaves a membrane-associated TNF-α (tumor necrosis factor alpha) and produces a soluble TNF-α, and is therefore referred to also as a TNF-α conversion enzyme (TACE). Soluble TNF-α causes inflammatory cytokine hypersecretion, cell apoptosis, obstruction of intracellular signal transduction, etc., and is to be a factor of bringing about cause and exacerbation of various diseases, as a result of primary and secondary tissue damages (see Non-Patent Reference 1). The pathological condition that TNF-α would participate in is considered to include typically rheumatoid arthritis (RA) as well as systemic lupus erythematosus (SLE), Crohn's disease, Behcet's disease, multiple sclerosis, Sjogren's syndrome, sepsis, acute infection, asthma, atopic dermatitis, psoriasis, etc.

ADAM17 (TACE) takes, as a substrate therefor, transforming growth factor (TGF)-α, heparin-binding EGF-like growth factor (HB-EGF), etc., in addition to the above-mentioned TNF-α. TGF-α is highly expressed in some human cancers, and is activated after released from cell membranes by the action of ADAM17 thereon. Regarding HB-EGF, when the transmembrane form thereof is cleaved by protease on the surface of a cell, this releases an EGF-like domain-containing extracellular domain and gives a soluble HB-EGF. It is known that the soluble HB-EGF is released from various tissues and cells such as epidermal cells, cardiocytes, vascular endothelial cells, smooth muscle cells, macrophages, etc., and causes cell growth and differentiation, inflammatory reaction, etc.

Consequently, a compound that inhibits ADAM17 is considered to be a promising therapeutic agent for various inflammatory disorders, various cancers, etc., and heretofore various studies have been made about ADAM17 inhibitors (see Non-Patent References 2 and 3, and Patent References 1 to 17).

As a substrate for ADAM10, another membrane-associated protease that belongs to the ADAM. family like ADAM17, there are Notch that participates in cancer progression, E-cadherin, epidermal growth factor (EGF), erythroblastic leukemia viral oncogene homolog 2 (ErbB2), etc., and it is reported that ADAM10 also releases TNF-α and HB-EGF, common to ADAM17. From these, it is suggested that ADAM10 would also acceleratingly participate in progression of pathological condition in disorders such as cancers, inflammations and others in which multiple factors would complexly interrelate with each other. Patent Reference 18 discloses an ADAM10 inhibitor; however, the compounds disclosed in Patent Reference 18 greatly differ from the compounds of the present invention in point of the structures thereof.

CITATION LIST

Patent References

Patent Reference 1: WO2008/038841
Patent Reference 2: WO2007/084455
Patent Reference 3: WO2007/068474
Patent Reference 4: WO2005/085232
Patent Reference 5: WO2004/056766
Patent Reference 6: WO2008/142376
Patent Reference 7: WO2008/038841
Patent Reference 8: WO2006/019768
Patent Reference 9: WO2006/066693
Patent Reference 10: WO2007/107663
Patent Reference 11: WO2007/008037
Patent Reference 12: WO2007/027718
Patent Reference 13: WO2007/084451
Patent Reference 14: WO2007/021803
Patent Reference 15: WO2007/084415
Patent Reference 16: WO2004/006927
Patent Reference 17: WO2003/022801
Patent Reference 18: WO2003/051825

Non-Patent References

Non-Patent Reference 1: Aggarwall B. B., Puri R. K., eds. 1995. Human Cytokines: Their Role in Disease and Therapy. Cambridge, Mass., USA: Blackwell Sci.

Non-Patent Reference 2: Nelson, F. C. et al., Exp. Opin. Invest. Drugs 1999, 8, 383-392

Non-Patent Reference 3: Newton, R. C. et al., J. Med. Chem. 1999, 42, 2295-2314

SUMMARY OF THE INVENTION

Problems that the Invention is to Solve

An object of the present invention is to provide a novel compound or its salt which has ADAM17 inhibitory activity, for treating or preventing various disorders in which ADAM17 is considered to participate, and to provide a medicament that contains the compound or its salt as an active ingredient therein.

Means for Solving the Problems

As a result of assiduous studies that the present inventors have made for the purpose of solving the above-mentioned problems, the inventors have found that an N-hydroxyformamide derivative having a specific structure has an excellent ADAM17-inhibitory activity, and have completed the present invention on the basis of this finding.

Specifically, the invention relates to the following:
(1) A compound represented by the following general formula (I), or a salt thereof, or a solvate thereof:

[Chemical Formula 1]

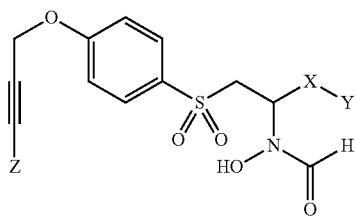

wherein X represents a phenylene group;
Y represents a hydrogen atom, or —$(CH_2)_m R^1$;
m indicates an integer of from 0 to 4;
$R^1$ represents:

[Chemical Formula 2]

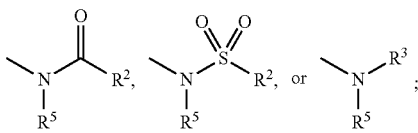

$R^2$ represents an optionally-substituted C1-C6 alkyl group, an optionally-substituted aryl group, or a C1-C6 alkoxy group;
$R^3$ and $R^4$ each independently represent a hydrogen atom, a C1-C6 alkyl group, or $R^3$ and $R^4$ may form a nitrogen-containing hetero ring along with the nitrogen atom adjacent thereto;
$R^5$ represents a hydrogen atom, a C1-C6 alkyl group or a C1-C6 alkylsulfonyl group;
Z represents a hydrogen atom or a C1-C6 alkyl group;
(2) The compound or a salt thereof or a solvate thereof described in the above (1), wherein the compound represented by the general formula (I) is the following:
N-[2-(4-but-2-ynyloxybenzenesulfonyl)-1-(4-diethylaminomethylphenyl)ethyl]-N-hydroxyformamide,
N-[2-(4-but-2-ynyloxybenzenesulfonyl)-1-(4-dimethylaminomethylphenyl)ethyl]-N-hydroxyformamide,
N-{4-[2-(4-but-2-ynyloxybenzenesulfonyl)-1-(formylhydroxyamino)ethyl]benzyl}-2-methoxyacetamide,
N-{4-[2-(4-but-2-ynyloxybenzenesulfonyl)-1-(formylhydroxyamino)ethyl]benzyl}methanesulfonamide,
N-{4-[2-(4-but-2-ynyloxybenzenesulfonyl)-1-(formylhydroxyamino)ethyl]benzyl}benzamide,
N-[2-(4-but-2-ynyloxybenzenesulfonyl)-1-(4-morpholin-4-ylmethylphenyl)ethyl]-N-hydroxyformamide,
N-hydroxy-N-[1-(4-morpholin-4-ylmethylphenyl)-2-(4-pent-2-ynyloxybenzenesulfonyl)ethyl]formamide,
N-[2-(4-but-2-ynyloxybenzenesulfonyl)-1-(4-dimethylaminophenyl)ethyl]-N-hydroxyformamide,
N-[2-(4-but-2-ynyloxybenzenesulfonyl)-1-(3-dimethylaminophenyl)ethyl]-N-hydroxyformamide,
N-[2-(4-but-2-ynyloxybenzenesulfonyl)-1-(2-dimethylaminophenyl)ethyl]-N-hydroxyformamide,
N-[2-(4-but-2-ynyloxybenzenesulfonyl)-1-(4-piperidin-1-ylmethylphenyl)ethyl]-N-hydroxyformamide,
N-[2-(4-but-2-ynyloxybenzenesulfonyl)-1-(3-piperidin-1-ylmethylphenyl)ethyl]-N-hydroxyformamide,
N-[2-(4-but-2-ynyloxybenzenesulfonyl)-1-(3-morpholin-4-ylmethylphenyl)ethyl]-N-hydroxyformamide,
N-[2-(4-but-2-ynyloxybenzenesulfonyl)-1-{4-[(ethylmethylamino)methyl]phenyl]ethyl}-N-hydroxyformamide,
N-(2-(4-but-2-ynyloxybenzenesulfonyl)-1-{3-[(ethylmethylamino)methyl]phenyl}ethyl)-N-hydroxyformamide,
N-{4-[2-(4-but-2-ynyloxybenzenesulfonyl)-1-(formylhydroxyamino)ethyl]benzyl}-N-methylmethanesulfonamide,
N-{4-[2-(4-but-2-ynyloxybenzenesulfonyl)-1-(formylhydroxyamino)ethyl]benzyl}-4-methylbenzenesulfonamide,
N-{4-[2-(4-but-2-ynyloxybenzenesulfonyl)-1-(formylhydroxyamino)ethyl]benzyl}-4,N-dimethylbenzenesulfonamide,
N-{4-[2-(4-but-2-ynyloxybenzenesulfonyl)-1-(formylhydroxyamino)ethyl]benzyl}-N-methylsulfonylmethanesulfonamide,
N-{2-(4-but-2-ynyloxybenzenesulfonyl)-1-[4-(2-dimethylaminoethyl)phenyl]ethyl}-N-hydroxyformamide,
N-{2-(4-but-2-ynyloxybenzenesulfonyl)-1-[4-(2-morpholin-4-ylethyl)phenyl]ethyl}-N-hydroxyformamide,
N-(2-{4-[2-(4-but-2-ynyloxybenzenesulfonyl)-1-(formylhydroxyamino)ethyl]phenyl}ethyl)methanesulfonamide,
N-{2-(4-but-2-ynyloxybenzenesulfonyl)-1-[4-(3-dimethylaminopropyl)phenyl]ethyl}-N-hydroxyformamide,
N-{2-(4-but-2-ynyloxybenzenesulfonyl)-1-[4-(3-diethylaminopropyl)phenyl]ethyl}-N-hydroxyformamide,
N-{2-(4-but-2-ynyloxybenzenesulfonyl)-1-[4-(3-morpholin-4-ylpropyl)phenyl]ethyl}-N-hydroxyformamide,
N-{2-(4-but-2-ynyloxybenzenesulfonyl)-1-[4-(4-morpholin-4-ylbutyl)phenyl]ethyl}-N-hydroxyformamide,
N-{4-[1-(formylhydroxyamino)-2-(4-pent-2-ynyloxybenzenesulfonyl)ethyl]benzyl}methanesulfonamide, or
N-{4-[1-(formylhydroxyamino)-2-(4-oct-2-ynyloxybenzenesulfonyl)ethyl]benzyl}methanesulfonamide;
(3) A medicament containing, as an active ingredient therein, a compound or a salt thereof or a solvate thereof described in the above (1) or (2);
(4) The medicament according to the above (3), which is an ADAM17 inhibitor;
(5) The medicament according to the above (3) or (4), which is an ADAM10 inhibitor;
(6) The medicament according to the above (3), which is a preventive agent or a treatment agent for rheumatoid arthritis, systemic lupus erythematosus, Crohn's disease, Behcet's disease, multiple sclerosis, Sjogren's syndrome, sepsis, acute infection, asthma, atopic dermatitis, psoriasis, or cancer;
(7) A pharmaceutical composition comprising the compound or a salt thereof or a solvate thereof described in the above (1) or (2), and a pharmacologically-acceptable carrier;
(8) A method of treating or preventing rheumatoid arthritis, systemic lupus erythematosus, Crohn's disease, Behcet's disease, multiple sclerosis, Sjogren's syndrome, sepsis, acute infection, asthma, atopic dermatitis, psoriasis or cancer, which comprising administering the compound or a salt thereof or a solvate thereof described in the above (1) or (2);
(9) Use of the compound or a salt thereof or a solvate thereof described in the above (1) or (2), in the manufacture of a pharmaceutical preparation for treating or preventing rheumatoid arthritis, systemic lupus erythematosus, Crohn's disease, Behcet's disease, multiple sclerosis, Sjogren's syndrome, sepsis, acute infection, asthma, atopic dermatitis, psoriasis or cancer; etc.

In the following description, the compound represented by the general formula (I) or a salt thereof or a solvate thereof is collectively referred to as "N-hydroxyformamide derivative of the invention".

Advantage of the Invention

The novel N-hydroxyformamide derivative of the invention has an excellent ADAM17-inhibitory activity as concretely described in Test Examples given hereinunder. Accordingly, the N-hydroxyformamide derivative of the invention is useful as an active ingredient of a preventive and treatment agent for disorders which ADAM17 participate in.

MODE FOR CARRYING OUT THE INVENTION

In the following, the N-hydroxyformamide derivative of the invention is described in detail. The description of the constitutive elements of the invention given hereinunder is for some typical embodiments or specific examples of the invention; however, the invention should not be limited to such embodiments or specific examples. In this description, the numerical range expressed by the wording "a number to another number" means the range that falls between the former number indicating the lower limit of the range and the latter number indicating the upper limit thereof.

N-hydroxyformamide Derivative of the Invention

First described are the substituents in the above-mentioned general formula (I). In the description of the substituents, "C1-C6" and "C6-C14" each mean that the carbon number falls within a range of from 1 to 6, and from 6 to 14, respectively.

"C1-C6 alkyl group" of "optionally-substituted C1-C6 alkyl group" in $R^2$, $R^3$, $R^4$, $R^5$ and Z means a linear or branched C1-C6 alkyl group, and its specific examples include a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, an n-hexyl group, etc.

The substituent in the above-mentioned "optionally-substituted C1-C6 alkyl group" includes a hydroxyl group, a halogen atom, a cyano group, a nitro group, a C1-C6 alkoxy group, a carboxyl group, a C1-C6 alkoxycarbonyl group, etc. At least one or more of these may be substituted in any and every substitutable position. In case where the compound has multiple substituents, the substituents may be the same or different, and may be substituted on the same carbon atom or on different carbon atoms.

"Halogen atom" means a fluorine atom, a chlorine atom, a bromine atom, an iodine atom.

"C1-C6 alkoxy group" means an alkoxy group in which the alkyl moiety is has the same meaning as that of the above-mentioned "C1-C6 alkyl group", for which, for example, there is mentioned a linear or branched alkoxy group such as a methoxy group, an ethoxy group, an n-propoxy group, an isopropoxy group, an n-butoxy group, an isobutoxy group, a tert-butoxy group, a sec-butoxy group, an n-pentyloxy group, a tert-amyloxy group, a 3-methylbutoxy group, a neopentyloxy group, an n-hexyloxy group, etc.

"C1-C6 alkoxycarbonyl group" means one in which the alkyl moiety excluding the oxycarbonyl moiety therein is a linear or branched C1-C6 alkyl group, including, for example, a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, a sec-butoxycarbonyl group, an n-pentyloxycarbonyl group, a tert-amyloxycarbonyl group, a 3-methylbutoxycarbonyl group, a neopentyloxycarbonyl group, an n-hexyloxycarbonyl group, etc.

"Nitrogen-containing ring" which $R^3$ and $R^4$ form along with the nitrogen atom adjacent thereto includes, for example, a 5- to 7-membered nitrogen-containing hetero ring which contains at least one nitrogen atom in addition to the carbon atom as the ring-constituting atom and may further contain one or two hetero atoms selected from an oxygen atom, a sulfur atom and a nitrogen atom. Preferred examples of the nitrogen-containing hetero ring include a piperidine ring, a piperazine ring, a morpholine ring, a thiomorpholine ring, a pyrrolidine ring, an imidazolidine ring, etc.

"Aryl group" of "optionally-substituted aryl group" in $R^2$ means an aromatic carbon ring, preferably a C6-C14 aromatic carbon ring, and includes, for example, a phenyl group, a naphthyl group, etc.

The substituent on the aromatic ring of the above-mentioned "optionally-substituted aryl group" includes a hydroxyl group, a halogen atom, a cyano group, a nitro group, a trifluoromethyl group, an optionally-substituted C1-C6 alkyl group, a C1-C6 alkoxy group, a carboxyl group, a C1-C6 alkoxycarbonyl group, etc. At least one or more of these may be substituted in any and every substitutable position. In case where the compound has multiple substituents, the substituents may be the same or different, and may be substituted on the same carbon atom or on different carbon atoms. In this, "halogen atom", "optionally-substituted C1-C6 alkyl group", "C1-C6 alkoxy group" and "C1-C6 alkoxycarbonyl group" have the same meanings as above.

"C1-C6 alkylsulfonyl group" in $R^5$ means an alkylsulfonyl group in which the alkyl moiety has the same meaning as that of the above-mentioned "C1-C6 alkyl group", including, for example, a methanesulfonyl group, an ethanesulfonyl group, etc.

In case where the compound represented by the general formula (I) has an asymmetric carbon, racemates and diastereomers thereof and also individual optical active forms of the compound are all included in the invention. In case where the compound has a geometric isomer, the (E) form and the (Z) form thereof and also the mixture thereof are all included in the invention.

Not specifically defined, the salt of the compound represented by the general formula (I) may be any pharmaceutically-acceptable salt thereof, including, for example, salts with an inorganic base, salts with an organic base, salts with an organic acid, salts with an inorganic acid, salts with an amino acid, etc. Examples of the salts with an inorganic base include alkali metal salts and alkaline earth metal salts such as lithium salts, sodium salts, potassium salts, calcium salts, magnesium salts, etc. Examples of the salts with an organic base include triethylamine salts, pyridine salts, ethanolamine salts, cyclohexylamine salts, dicyclohexylamine salts, dibenzylethanolamine salts, etc. Examples of the salts with an organic acid include formates, acetates, tartrates, maleates, succinates, lactates, malates, ascorbates, oxalates, glycolates, phenylacetates, methanesulfonates, etc. Examples of the salts with an inorganic acid include hydrochlorides, hydrobromides, phosphates, sulfamates, nitrates, etc. Examples of the salts with an amino acid include glycine salts, alanine salts, arginine salts, glutamates, aspartates, etc.

The compound represented by the general formula (I) may have a form of prodrug. Examples of prodrug include methyl ester, ethyl ester and aminoalkyl ester derivatives at the carboxyl group of the compound of the general formula (I), acetate, formate and benzoate derivatives at the hydroxyl group and the amine functional group of the compound of the general formula (I), etc., to which, however, the invention is not limited.

Production Method for N-Hydroxyformamide Derivative of the Invention

The compound represented by the above-mentioned general formula (I) can be produced according to various methods but may be efficiently produced according to the method mentioned below.

Specific examples of the "protective group" for use in the production method mentioned below include a tert-butyl group, a benzyl group, an o-methylbenzyl group, a p-nitrobenzyl group, a p-methoxybenzyl group, an o-chlorobenzyl group, a 2,4-dichlorobenzyl group, a p-bromobenzyl group, an allyl group, a tert-butoxycarbonyl group, a benzyloxycarbonyl group, an o-methylbenzyloxycarbonyl group, a p-nitrobenzyloxycarbonyl group, a p-methoxybenyloxycarbonyl group, an o-chlorobenzyloxycarbonyl group, a 2,4-dichlorobenzyloxycarbonyl group, a p-bromobenzyloxycarbonyl group, an allyloxycarbonyl group, a tert-butyldimethylsilyl group, a tert-butyldiphenylsilyl group, a triethylsilyl group, a trimethylsilyl group, a triisopropylsilyl group, a methoxymethyl group, a tetrahydropyranyl group, carbonyl protective groups (for example, protective groups with ethanediol, propanediol, mercaptoethanol, mercaptopropanol, ethanedithiol, propanedithiol, etc.), etc.

The compound represented by the general formula (I) can be produced, for example, through the reaction of the following step 1 and step 2.

Scheme 1:

[Chemical Formula 3]

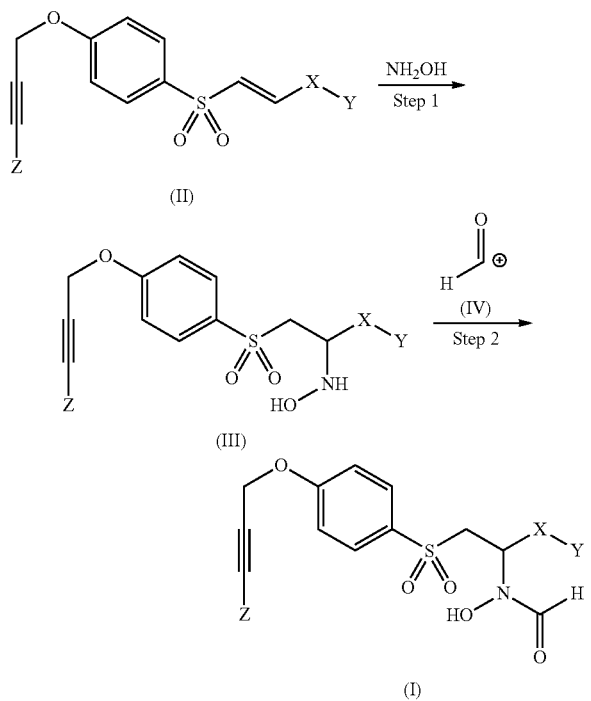

(In the formulae, X, Y and Z have the same meanings as mentioned above.)

<Step 1>

In the step 1, hydroxylamine or its salt is added to the compound (II) to produce the compound represented by the general formula (III). In case where hydroxylamine is a salt thereof (hydrochloride, acetate, etc.), the addition reaction is attained in the presence of an inorganic base such as potassium carbonate, sodium carbonate, sodium hydrogen carbonate, sodium hydroxide, potassium hydroxide, lithium hydroxide, etc. Not specifically defined, the reaction solvent may be any solvent not significantly interfering with the reaction, but is preferably water, tetrahydrofuran, cyclopentyl methyl ether, acetonitrile, 1,4-dioxane, diethyl ether or their mixed solvent, etc.

Not specifically defined, the reaction temperature may be generally from 0 to 100° C., and the reaction time is preferably from 2 hours to 1 week.

<Step 2>

In the step 2, the compound (III) obtained in the step 1 is condensed with the intermediate represented by the general formula (IV) to produce the compound represented by the general formula (I). The intermediate (IV) is an reactive intermediate to be obtained from a mixed acid anhydride with formic acid (mixed acid anhydride of formic acid and acetic acid, etc.), pentafluorophenyl formate, or formic acid and a carbodiimide (dicyclohexylcarbodiimide, diisopropylcarbodiimide or water-soluble carbodiimide). For smoothly attaining the reaction, an organic base such as triethylamine, diisopropylethylamine, pyridine, lutidine, collidine, dimethylaminopyridine or the like may be made to coexist in the system. Adding 1-hydroxybenzotriazole and/or 4-dimethylaminopyridine to some of these cases (especially where the reactive intermediate is obtained from carbodiimide) could promote the reaction. Not specifically defined, the reaction solvent may be any solvent not significantly interfering with the reaction, but is preferably chloroform, methylene chloride, tetrahydrofuran, acetonitrile, cyclopentyl methyl ether, 1,4-dioxane, dimethylformamide, dimethyl sulfoxide, pyridine, etc. Not specifically defined, the reaction temperature may be generally from 0 to 100° C., and the reaction time is preferably from 1 to 24 hours. In this step, a CHO group may be added to also to the hydroxyl group of the hydroxylamino group, depending on the chemical properties of the starting materials; but in such a case, the product may be processed with a lower alcohol in an acidic, basic or neutral condition to be converted into the intended product, compound (I). The lower alcohol is preferably methanol, ethanol, propanol, etc. An auxiliary solvent may be used here, and when used, the auxiliary solvent is not specifically defined.

Needless to say, depending on the properties of X, Y and Z, it is necessary to previously use the corresponding protective group in the reaction of the above-mentioned step 1 and step 2 and to remove the protective group after the reaction. In case where the group is not protected, the yield in the next step and further in the next step after that next step may lower and the intermediate may be difficult to handle.

The above-mentioned compound (II) may be produced according to the process of the step 3 to step 5, as mentioned below.

Scheme 2:

[Chemical Formula 4]

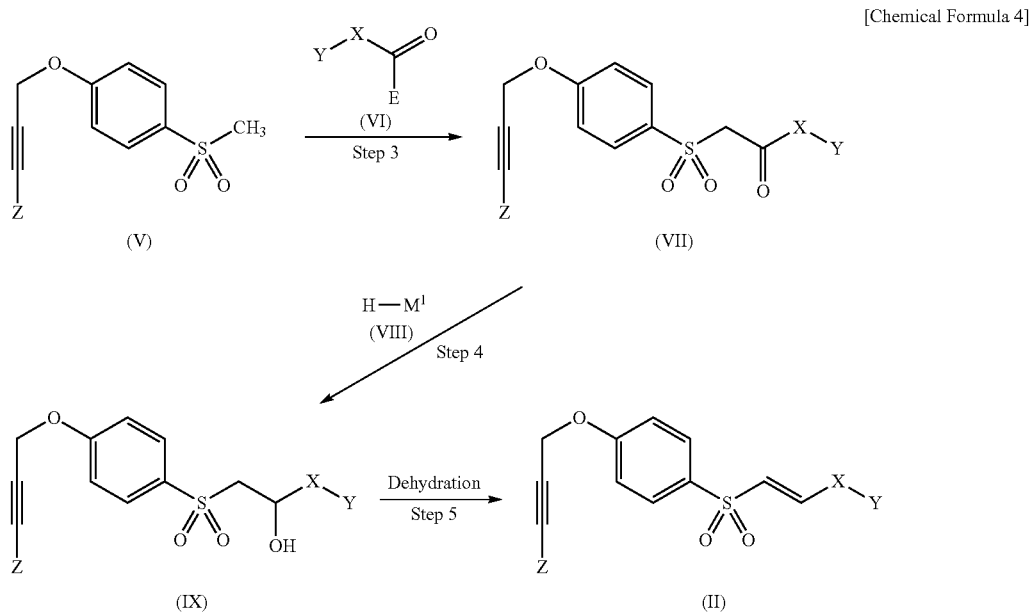

(In the formulae, X, Y and Z have the same meanings as above; E represents a releasing functional group such as a C1-C6 alkoxy group, a halogen atom, an N,O-dimethylhydroxyamino group or the like; $M^1$ represents Li, $CeCl_2$, $NaBH_3$, $LiBH_3$, $LiBEt_3$, $KBEt_3$, $LiB[CH(CH_3)C_2H_5]_3$, $KB[CH(CH_3)C_2H_5]_3$, $Al[CH(CH_2)C_2H_5]_2$ or the like; Et represents an ethyl group.)

<Step 3>

In the step 3, the compound represented by the general formula (V) is converted into an anion with a base, and then reacted with the compound represented by the general formula (VI) to produce the compound (VII). The base to be used includes lithium diisopropylamide, lithium (bistrimethylsilyl)amide, lithium tetramethylpiperazide, sodium (bistrimethylsilyl)amide, potassium (bistrimethylsilyl)amide, n-butyllithium, sec-butyllithium, tert-butyllithium, etc. One alone or, as the case may be, two or more of these may be used either singly or as combined. Not specifically defined, the reaction solvent may be any one not significantly interfering with the reaction, but is preferably tetrahydrofuran, cyclopentyl methyl ether, tetrahydrofuran, diethyl ether, tert-butyl methyl ether, or their mixed solvent, etc.

The reaction temperature may be generally from −100 to 40° C. and the reaction time is preferably from 1 to 12 hours. In this step, the compound (II) may be produced depending on the chemical properties of the compound (VI), which, however, causes no problem in consideration of the intended production object.

<Step 4>

In the step 4, the compound (VII) obtained in the step 3 is reacted with the compound represented by the general formula (VIII) to produce the compound represented by the general formula (IX). The reaction solvent is, when the compound (VIII) is sodium borohydride or lithium borohydride, preferably methanol, ethanol, isopropanol, tetrahydrofuran, cyclopentyl methyl ether, dichloromethane, chloroform or their mixture, etc.; but when the compound (VIII) is any other than those two, the reaction solvent is preferably tetrahydrofuran, cyclopentyl methyl ether, tetrahydropyran, diethyl ether, tert-butyl methyl ether or their mixed solvent, etc. The reaction temperature may be generally from −100 to 30° C. and the reaction time is preferably from 1 to 12 hours.

During or after the reaction of the step 4, the hydroxyl group may be spontaneously eliminated from the formed compound (IX) whereby the compound may be partly or wholly converted into the compound (II). In the case of partial conversion, the step 5 may be carried out without separating the converted compound; and in the case of complete conversion, the step 5 may be omitted.

<Step 5>

In the step 5, the compound (IX) obtained in the step 4 may be dehydrated to produce the compound (II). The dehydration reaction is attained by a combination of a hydroxyl group activator and an organic base. The hydroxyl group activator includes methanesulfonyl chloride, p-toluenesulfonyl chloride, benzenesulfonyl chloride, methanesulfonyl chloride, thionyl chloride, surfuryl chloride, phosphorus pentachloride, etc. The organic base includes triethylamine, diisopropylethylamine, diazabicycloundecene, diazabicyclononene, pyridine, dimethylaminopyridine, lutidine, collidine, etc. Preferred is a combination of methanesulfonyl chloride and triethylamine. As other dehydration reagents, there may be mentioned triphenylphosphine-diethyl azodicarboxylate, triphenylphosphine-diisopropyl azocarboxylate, tri-n-butylphosphine-diethyl azodicarboxylate, tri-n-butylphosphine-diisopropyl azocarboxylate, etc. The reaction solvent may be any one not significantly interfering with the reaction, but is preferably chloroform, methylene chloride, tetrahydrofuran, cyclopentyl methyl ether, acetonitrile, 1,4-dioxane, dimethyl formamide, etc. Not specifically defined, the reaction temperature may be generally from 0 to 100° C., and the reaction time is preferably from 1 to 24 hours.

Needless to say, depending on the properties of X, Y and Z, it is necessary to previously use the corresponding protective group in the reaction of the above-mentioned step 3 to step 5 and to remove the protective group after the reaction.

The compound (V) may be produced according to the step 6 mentioned below.

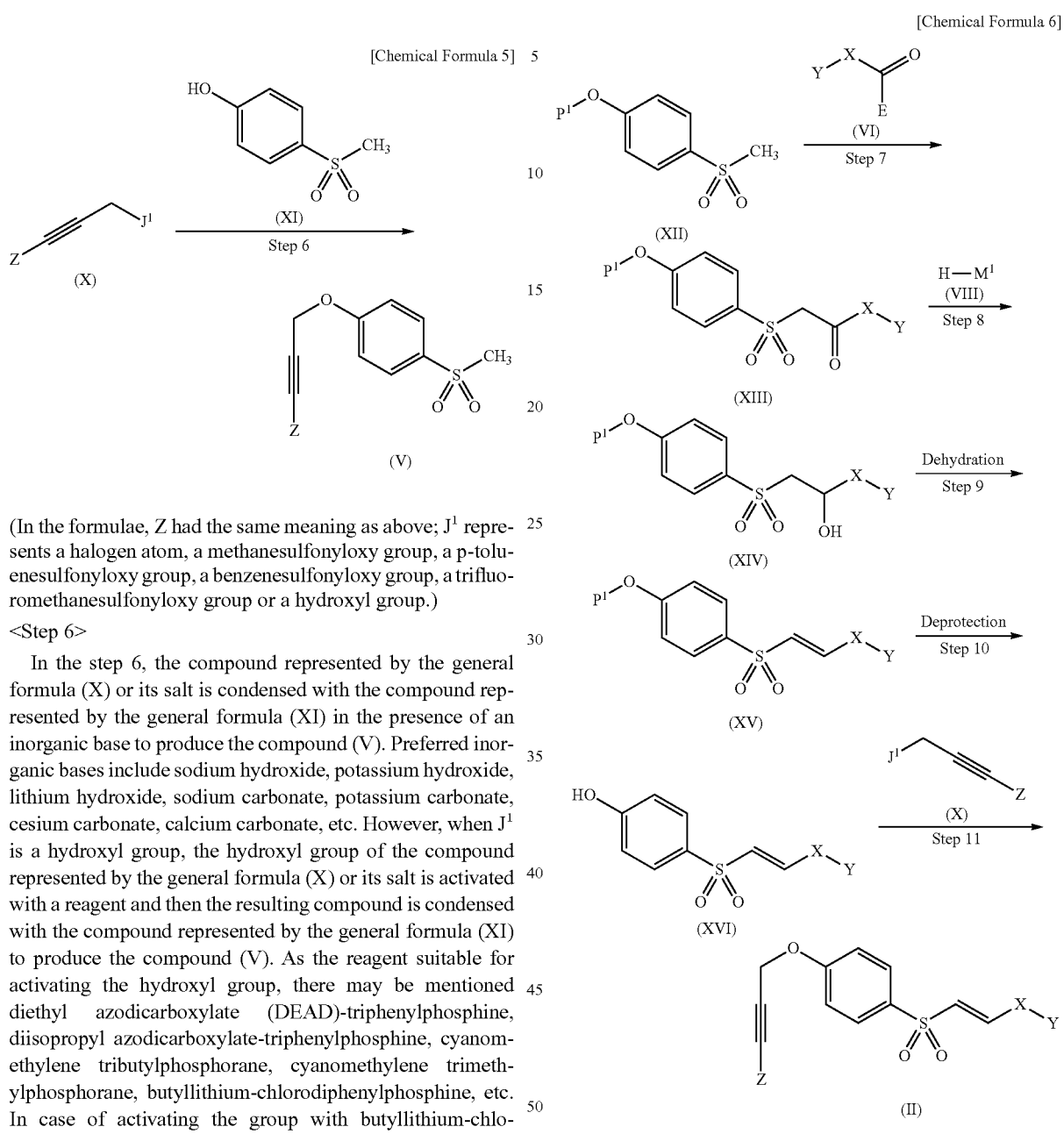

Scheme 4:

(In the formulae, Z had the same meaning as above; $J^1$ represents a halogen atom, a methanesulfonyloxy group, a p-toluenesulfonyloxy group, a benzenesulfonyloxy group, a trifluoromethanesulfonyloxy group or a hydroxyl group.)

<Step 6>

In the step 6, the compound represented by the general formula (X) or its salt is condensed with the compound represented by the general formula (XI) in the presence of an inorganic base to produce the compound (V). Preferred inorganic bases include sodium hydroxide, potassium hydroxide, lithium hydroxide, sodium carbonate, potassium carbonate, cesium carbonate, calcium carbonate, etc. However, when $J^1$ is a hydroxyl group, the hydroxyl group of the compound represented by the general formula (X) or its salt is activated with a reagent and then the resulting compound is condensed with the compound represented by the general formula (XI) to produce the compound (V). As the reagent suitable for activating the hydroxyl group, there may be mentioned diethyl azodicarboxylate (DEAD)-triphenylphosphine, diisopropyl azodicarboxylate-triphenylphosphine, cyanomethylene tributylphosphorane, cyanomethylene trimethylphosphorane, butyllithium-chlorodiphenylphosphine, etc. In case of activating the group with butyllithium-chlorodiphenylphosphine, a quinone compound such as 2,6-dimethyl-1,4-benzoquinone, tetrafluoro-1,4-benzoquinone or the like is added to the system.

Not specifically defined, the reaction solvent may be any one not significantly interfering with the reaction, but is preferably water, methanol, ethanol, tert-butanol, tetrahydrofuran, cyclopentyl methyl ether, acetonitrile, diethyl ether, dimethyl ether, dichloromethane, 1,4-dioxane, 2-methoxyethanol, N,N-dimethylformamide, or their mixed solvent, etc. Not specifically defined, the reaction temperature may be generally from −80 to 120° C., and the reaction time is preferably from 1 to 24 hours.

The above-mentioned compound (II) may also be produced through the reaction of the following step 7 to step 11, as mentioned below.

(In the formulae, X, Y, Z, E, $M^1$ and $J^1$ are the same as mentioned above; and $P^1$ represents a hydroxyl-protective group.)

<Step 7>

In the step 7, the compound represented by the general formula (XII) is converted into an anion with a base, and then reacted with the compound (VI) to produce the compound (XIII), like in the step 3.

<Step 8>

In the step 8, the compound represented by the general formula (XIII) is reacted with the compound represented by the general formula (VIII) to produce the compound (XIV), like in the step 4.

Needless to say, depending on the properties of X and Y, it is necessary to previously use the corresponding protective group in the reaction of the above-mentioned step 7 and step 8 and to remove the protective group after the reaction.

<Step 9>

In the step 9, the compound (XIV) is dehydrated to produce the compound (XV), like in the step 5.

In the step 9, the protective group $P^1$ may be spontaneously removed from the formed compound whereby the compound may be partly or wholly converted into the compound (XVI). In the case of partial conversion, the step 10 may be carried out without separating the converted compound; and in the case of complete conversion, the step 10 may be omitted.

<Step 10>

In the step 10, the compound represented by the general formula (XV) is deprotected according to any known method depending on the type of the protective group $P^1$ therein, thereby producing the compound represented by the general formula (XVI).

<Step 11>

In the step 11, the compound (XVI) is condensed with the compound represented by the general formula (X) or its salt to produce the compound (II), like in the step 6.

The N-hydroxyformamide derivative of the invention, thus produced according to the above-mentioned method, may be isolated and purified as a free compound thereof, or as its salt, its hydrate or its various types of solvates such as an ethanolate thereof, or as a polymorphic form thereof. The pharmaceutically-acceptable salt of the compound of the general formula (I) can be produced according to conventional salt-forming reaction. The isolation and purification may be attained by chemical operation of extractive fractionation, crystallization, various types of fractionation chromatography, etc. An optical isomer may be obtained as stereochemically pure isomer by selecting suitable starting materials or by optical resolution of racemic compounds.

Use of N-Hydroxyformamide Derivative of the Invention

The N-hydroxyformamide derivative of the invention exhibits an excellent ADAM17-inhibitory activity and is useful as therapeutic agents for various ADAM17-related disorders including, for example, autoimmune diseases such as rheumatoid arthritis (RA), osteoarthritis (OA), systemic lupus erythematosus, multiple sclerosis, Behcet's disease, Sjogren's syndrome, etc., and various organ inflammations associated with these; allergic disorders such as asthma, atopic dermatitis, nasal obstruction, rhinitis, etc.; inflammatory bowel diseases including Crohn's disease, etc.; nephritis, hepatitis, central nervous system inflammatory diseases; dermatitis-related diseases such as psoriasis, scleroderma, sarcoidosis, etc.; periodontitis, cardiovascular disorders, arteriosclerosis, diabetes, myasthenia gravis, acute infections, fever, anemia, sepsis, ischemia-reperfusion injury, malaria, mycobacterial infection, meningitis, congestive cardiac failure, fibrosis, cachexia, graft rejection, angiogenesis-related disorders, ankylosing spondylitis, psoriatic arthritis, adult-onset Still's disease, Wegener granulomatosis, polymyositis, dermatomyositis, sciatic neuralgia, complex regional pain syndrome, radiation injury, hyperoxic alveolar injury, HIV, glaucoma, idiopathic pulmonary fibrosis, bronchopulmonary dysplasia, retinal disease, osteoporosis, renal ischemia, myocardial infarction, cerebral stroke, cerebral ischemia, glomerulonephritis, idiopathic fibrosing alveolitis, vasculitis, reversible airway obstruction, adult hyperpnea syndrome, chronic obstructive pulmonary disease (COPD), bronchitis, various cancers, allograft damage prevention, tumor growth or metastasis inhibition, etc.

Of the N-hydroxyformamide derivative of the invention, that having an ADAM17-inhibitory activity and additionally having an ADAM10-inhibitory activity is more useful as a therapeutic agent of disorders which ADAM17 and ADAM10 are related in common (for example, various cancers and inflammatory disorders such as rheumatoid arthritis, etc.).

The N-hydroxyformamide derivative of the invention is administered systemically or topically according to a process of oral, transdermal, transnasal, transtracheal, pulmonary, ophthalmic, intravenous, subcutaneous or rectal administration or the like. The dosage form can be suitably selected in accordance with the administration route, including, for example, tablets, troches, sublingual tablets, sugarcoated tablets, capsules, pills, powders, granules, liquids, emulsions, creams, ointments, jellies, suspensions, syrups, eye drops, nasal sprays, inhalants, suppositories, injections, etc. These preparations may be produced by incorporating thereinto an excipient, a preservative, a wetting agent, an emulsifier, a stabilizer, a dissolution aid or the like.

The dose of the N-hydroxyformamide derivative of the invention may be suitably determined depending on the subject to which the compound is administered, the administration route, the symptom, etc., and for example, in a case of oral administration to an adult patient, the dose of the compound of the active ingredient to be administered thereto is generally within a range of from about 0.1 to 100 mg/kg, preferably from 1 to 40 mg/kg, and preferably once to three times a day.

The ADAM17-inhibitory activity of the N-hydroxyformamide derivative of the invention is preferably from 0.01 nM to 1000 nM in terms of the 50%-inhibitory concentration ($IC_{50}$) thereof.

EXAMPLES

Examples and Test Examples are shown below, by which the characteristics of the invention are described more concretely. In the following Examples, the material used, its amount and ratio, the details of the handling and the procedure may be suitably modified or changed not overstepping the spirit and the scope of the invention. Accordingly, the invention should not be limitatively interpreted by the Examples mentioned below.

The $^1$H-NMR spectra shown below were measured, using deuterated chloroform ($CDCl_3$) or deuterated dimethylsulfoxide (DMSO-$d_6$) as the solvent, using tetramethylsilane (TMS) as the internal standard and using a spectral meter ECA400 Model (400 MHz, by JEOL). Regarding the measurement data of the chemical shift, the δ value is expressed by ppm, and the J value of the coupling constant is by Hz. Of the abbreviations, s means singlet, d means doublet, t means triplet, q means quartet, dd means doublet doublet, m means multiplet, and br means broad. For low-resolution mass spectrometry (fast atom bombardment mass spectrometry, FAB-MS), used was JEOL's JMS-HX-110A Model; and for mass spectrometry (electrospray ionization mass spectrometry, ESI-MS), used was Thermofisher Scientific's Exactive.

Example 1

N-[2-(4-But-2-ynyloxybenzenesulfonyl)-1-(4-diehtylaminomethylphenyl)ethyl]-N-hydroxyformamide (I-1)

[Chemical Formula 7]

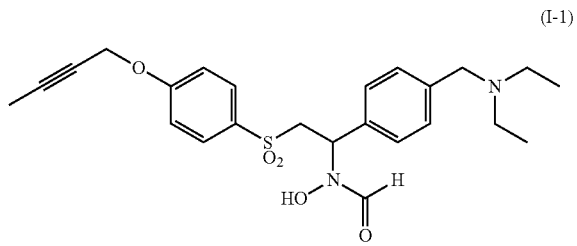

(I-1)

(1-1): 1-But-2-ynyloxy-4-methanesulfonylbenzene (V-1)

2.88 g (15.9 mmol) of 4-methylsulfonylphenol was added to and dissolved in a dimethylsulfoxide solution (30 mL) of 2.12 g (15.9 mmol) of 1-bromo-2-butyne, and then 2.64 g (19.1 mmol) of potassium carbonate was added thereto. After stirred for 6 hours, brine was added thereto and extracted with ethyl acetate. The organic layer was washed with brine, and dried over anhydrous magnesium sulfate. 3.39 g (15.11 mmol) of 1-but-2-ynyloxy-4-methanesulfonylbenzene (V-1) was obtained as a roughly-purified product (yield 95%). Its physical properties are shown below.

MS (FAB) m/z: 225 (M+H)$^+$.

$^1$H-NMR (CDCl$_3$): δ 7.88 (2H, m), 7.10 (2H, m), 4.73 (2H, m), 3.04 (3H, s), 1.87 (3H, t, J=2.3 Hz).

(1-2): tert-Butyl {4-[2-(4-but-2-ynyloxybenzenesulfonyl)acetyl]benzyl}carbamate (VII-1)

In an argon atmosphere at −78° C., 3.65 mL (7.29 mmol) of a hexane-heptane-ethylbenzene solution of 2.0 M lithium diisopropylamide was added to a tetrahydrofuran (70 mL) solution of 1.36 g (6.08 mmol) of the compound (V-1) obtained in the above (1-1), stirred for 30 minutes, and then 12.16 mL (12.16 mmol) of a tetrahydrofuran solution of 1.0 M lithium hexamethyldisilazide and 5 mL of a tetrahydrofuran solution of 1.61 g (6.08 mmol) of methyl 4-(tert-butoxycarbonylaminomethyl)benzoate were added thereto. After stirred at −78° C. for 5 minutes, this was gradually heated up to room temperature, and stirred for 1 hour. After brine was added thereto, this was extracted with ethyl acetate, and the organic layer was washed with brine. After dried over anhydrous magnesium sulfate, the solvent was evaporated away under reduced pressure. Purified by silica gel column chromatography (hexane/ethyl acetate=2/1→1/1), this gave 2.02 g (4.41 mmol) of tert-butyl {4-[2-(4-but-2-ynyloxybenzenesulfonyl)acetyl]benzyl}carbamate (VII-1) as a colorless molten caramel-like substance (yield 72%). Its physical properties are shown below.

MS (FAB) m/z: 480 (M+Na)$^+$.

$^1$H-NMR (CDCl$_3$): δ 7.93 (2H, br d, J=8.2 Hz), 7.81 (2H, m), 7.40 (2H, br d, J=8.2 Hz), 7.07 (2H, m), 4.72 (2H, m), 4.70 (2H, s), 4.39 (2H, m), 1.87 (3H, t, J=2.3 Hz), 1.57 (9H, s).

(1-3): tert-Butyl {4-[2-(4-but-2-ynyloxybenzenesulfonyl)-1-hydroxyethyl]benzyl}carbamate (IX-1)

At 0° C., 167 mg (4.41 mmol) of sodium borohydride was added to a methanol (50 mL) solution of 2.02 g (4.41 mmol) of the compound (VII-1) obtained in the above (1-2). After stirred for 2 hours and 30 minutes, brine and aqueous saturated ammonium chloride solution were added thereto. Methanol was evaporated away under reduced pressure, then the residue was extracted with ethyl acetate, and the organic layer was washed with brine, and dried over anhydrous magnesium sulfate. The solvent was evaporated away under reduced pressure to give 2.04 g (4.41 mmol) of tert-butyl {4-[2-(4-but-2-ynyloxybenzenesulfonyl)-1-hydroxyethyl]benzyl}carbamate (IX-1), as a roughly-purified amorphous solid substance (yield 99%). Its physical properties are shown below.

MS (FAB) m/z: 482 (M+Na)$^+$.

(1-4): tert-Butyl {4-[2-(4-but-2-ynyloxybenzenesulfonyl)vinyl]benzyl}carbamate (II-1a)

At 0° C., 0.7 mL (8.8 mmol) of methanesulfonyl chloride was added to a dichloromethane (45 mL) solution of 2.04 g (4.41 mmol) of the compound (IX-1) obtained in the above (1-3) and 3.1 mL (22.1 mmol) of triethylamine. After stirred for 3 hours and 30 minutes, brine was added thereto, and extracted with chloroform. The organic layer was washed with brine, and dried over anhydrous magnesium sulfate. The solvent was evaporated away under reduced pressure, and the residue was purified by silica gel column chromatography (chloroform/ethyl acetate=3/1) to give 1.77 g (4.00 mmol) of tert-butyl {4-[2-(4-but-2-ynyloxybenzenesulfonyl)vinyl]benzyl}carbamate (II-1a) as a colorless amorphous solid (yield 91%). Its physical properties are shown below.

$^1$H-NMR (CDCl$_3$): δ 7.87 (2H, d, J=8.7 Hz), 7.61 (1H, d, J=15 Hz), 7.43 (2H, J=8.2 Hz), 7.30 (2H, d, J=8.2 Hz), 7.10 (2H, d, J=8.7 Hz), 6.82 (1H, d, J=15 Hz), 4.88 (1H, m), 4.71 (2H, m), 4.33 (2H, m), 1.86 (3H, m), 1.45 (9H, s).

(1-5): 4-[(E)-2-(4-But-2-ynyloxybenzenesulfonyl)vinyl]benzylaminehydrochloride (II-1b)

At 0° C., 2 mL of 4 M-hydrochloric acid/dioxane was added to a methanol (5 mL) solution of 295 mg (0.67 mmol) of the compound (II-1a) obtained in the above (1-4), stirred for 10 minutes, heated up to room temperature, and stirred for 2 hours. The solvent was evaporated away under reduced pressure, then 20 mL of methanol was added thereto, and the solvent was again evaporated away under reduced pressure to give 4-[(E)-2-(4-but-2-ynyloxybenzenesulfonyl)vinyl]benzylamine hydrochloride (II-1b) as a colorless solid. Its physical properties are shown below.

$^1$H-NMR (DMSO-d$_6$): δ 7.85 (2H, d, J=8.7 Hz), 7.78 (2H, d, J=8.2 Hz), 7.52 (2H, d, J=8.2 Hz), 7.20 (2H, d, J=8.7 Hz), 4.87 (2H, m), 4.05 (2H, m), 1.83 (3H, m).

(1-6): {4-[(E)-2-(4-But-2-ynyloxybenzenesulfonyl)vinyl]benzyl}diethylamine (II-1c)

At 0° C., 1 mL of acetaldehyde, 212 mg (1.00 mmol) of sodium triacetoxyhydroborate and 3 drops of acetic acid were added to a methanol (6 mL) solution of the compound (II-1b)

obtained in the above (1-5), and then stirred at room temperature for 1 hour and 30 minutes. After brine and saturated aqueous sodium bicarbonate solution were added thereto, and the solvent was evaporated away under reduced pressure. This was extracted with chloroform, the organic layer was washed with brine and dried over anhydrous magnesium sulfate. The solvent was evaporated away under reduced pressure, and the residue was purified by silica gel column chromatography (chloroform/methanol=20/1→10/1) to give 111.7 mg (0.28 mmol) of {4-[(E)-2-(4-but-2-ynyloxybenzenesulfonyl)vinyl]benzyl}diethylamine (II-1c) as a pale yellow amorphous solid (two steps yield 42%). Its physical properties are shown below.

MS (FAB) m/z: 398 (M+H)+.

(1-7): N-[2-(4-But-2-ynyloxybenzenesulfonyl)-1-(4-diethylaminomethylphenyl)ethyl]hydroxylamine (III-1)

50% hydroxylamine solution (3 mL) was added to a tetrahydrofuran (8 mL) solution of 108 mg (0.27 mmol) of the compound (II-1c) obtained in the above (1-6), and stirred at room temperature for 25 hours. The reaction solution was evaporated under reduced pressure, and then water was added thereto and extracted with chloroform. The organic layer was washed with brine, dried over anhydrous magnesium sulfate, and concentrated under reduced pressure. 92.9 mg (0.22 mmol) of N-[2-(4-but-2-ynyloxybenzenesulfonyl)-1-(4-diethylaminomethylphenyl)ethyl]hydroxylamine (III-1) was obtained as a pale yellow amorphous solid (yield 81%). Its physical properties are shown below.

$^1$H-NMR (CDCl$_3$): δ 7.84 (2H, m), 7.27 (2H, m), 7.20 (2H, m), 7.07 (2H, m), 4.72 (2H, m), 3.75 (1H, m), 3.51 (2H, s), 3.33 (1H, m), 2.49 (4H, m), 1.87 (3H, s), 1.03 (6H, m).

(1-8): N-[2-(4-But-2-ynyloxybenzenesulfonyl)-1-(4-diethylaminomethylphenyl)ethyl]-N-hydroxyformamide (I-1)

1 mL of formic acid was cooled at 0° C., then 0.3 mL of acetic anhydride was dropwise added thereto and stirred for 30 minutes to prepare a formic acid/acetic acid mixed acid anhydride solution. At 0° C., 0.6 ml of the formic acid/acetic acid mixed acid anhydride solution prepared previously was added to a tetrahydrofuran (3 mL) solution of 92 mg (0.21 mmol) of the compound (III-1) obtained in the above (1-7), and stirred at room temperature for 4 hours. The reaction mixture was concentrated under reduced pressure, and then azeotroped with toluene. The obtained oily substance was dissolved in 2 mL of chloroform and 10 mL of methanol, and stirred for 12 hours. The solution was concentrated under reduced pressure, and the resulting oily substance was dissolved in chloroform and neutralized with saturated aqueous sodium bicarbonate solution added thereto. After extracted with chloroform, the extract was washed with brine and dried over anhydrous magnesium sulfate. Purifying by middle-pressure silica gel column chromatography (chloroform/methanol=95/5→75/25) gave 53.9 mg (0.11 mmol) of N-[2-(4-but-2-ynyloxybenzenesulfonyl)-1-(4-diethylaminomethylphenyl)ethyl]-N-hydroxyformamide (I-1) as a pale yellow amorphous solid (yield 52%). Its physical properties are shown below.

MS (FAB) m/z: 459 (M+H)+.

$^1$H-NMR (CDCl$_3$): δ 8.32 (0.6H, s), 8.10 (0.4H, s), 7.80-7.86 (2H, m), 7.21-7.30 (4H, m), 7.06-7.14 (2H, m), 5.65 (0.6H, m), 5.36 (0.4H, m), 4.74 (2H, br s), 4.20 (0.4H, m), 4.05 (0.6H, br t, J=13 Hz), 3.48-3.57 (3H, m), 2.46 (4H, m), 1.87 (3H, br s), 0.99 (6H, m).

Example 2

N-[2-(4-But-2-ynyloxybenzenesulfonyl)-1-(4-dimethylaminomethylphenyl)ethyl]-N-hydroxyformamide (I-2)

[Chemical Formula 8]

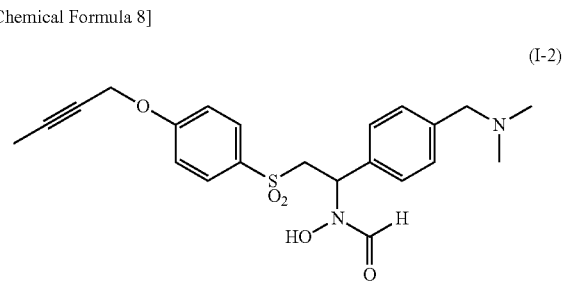

(I-2)

According to the same operation as in Example 1, the above-mentioned compound (I-2) was obtained.

MS (FAB) m/z: 431 (M+H)+.

$^1$H-NMR (CDCl$_3$): δ 8.28 (0.6H, s), 8.14 (0.4H, s), 7.79-7.91 (2H, m), 7.04-7.32 (6H, m), 5.69 (0.6H, m), 5.35 (0.4H, m), 4.74 (2H, br s), 4.18 (0.4H, m), 4.07 (0.6H, m), 3.47 (1H, m), 3.33 (2H, m), 2.11 (6H, s), 1.87 (3H, s).

Example 3

N-{4-[2-(4-But-2-ynyloxybenzenesulfonyl)-1-(formylhydroxyamino)ethyl]benzyl}-2-methoxyacetamide (I-3)

[Chemical Formula 9]

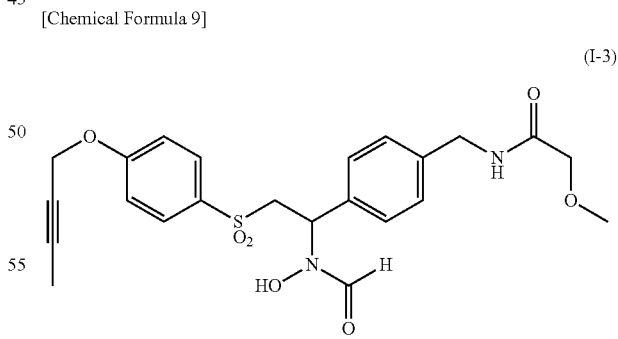

(I-3)

(3-1): N-{4-[2-(4-But-2-ynyloxybenzenesulfonyl)vinyl]benzyl}-2-methoxyacetamide (II-3)

At room temperature, 0.2 mL (1.85 mmol) of methoxyacetyl chloride was dropwise added to a pyridine solution (5 mL) of 283 mg (0.75 mmol) of the compound (II-1b) obtained in the above-mentioned Example 1 (1-5). After 2 days, brine was added thereto, extracted with ethyl acetate, and washed with brine. This was dried over anhydrous magnesium sulfate, the solvent was evaporated away under reduced pressure, and the residue was purified by silica gel column chromatography (chloroform/methanol=20/1→10/1) to give 296 mg (0.71 mmol) of the compound (II-3) as a pale yellow solid (yield 94%). Its physical properties are shown below.

MS (FAB) m/z: 414 (M+H)$^+$.

(3-2): N-{4-[2-(4-But-2-ynyloxybenzenesulfonyl)-1-(formylhydroxyamino)ethyl]benzyl}-2-methoxyacetamide (I-3)

According to the same process as in the above-mentioned Example 1 (1-7 and 1-8) but using the compound (II-3) obtained in the above (3-1), N-{4-[2-(4-but-2-ynyloxybenzenesulfonyl)-1-(formylhydroxyamino)ethyl]benzyl}-2-methoxyacetamide (I-3) was obtained. Its physical properties are shown below.

$^1$H-NMR (CDCl$_3$): δ 8.32 (0.6H, s), 8.09 (0.4H, s), 7.77-7.88 (2H, m), 7.20-7.31 (4H, m), 7.06-7.16 (2H, m), 5.65 (0.6H, m), 5.37 (0.4H, m), 4.75 (2H, br s), 4.39-4.47 (2H, m), 4.16 (0.4H, m), 4.03 (0.6H, br t), 3.93 (0.8H, br s), 3.90 (1.2H, br s), 3.46 (1H, m), 3.40 (3H, br s), 1.87 (3H, br s).

Example 4

N-{4-[2-(4-But-2-ynyloxybenzenesulfonyl)-1-(formylhydroxyamino)ethyl]benzyl}methanesulfonamide (I-4)

[Chemical Formula 10]

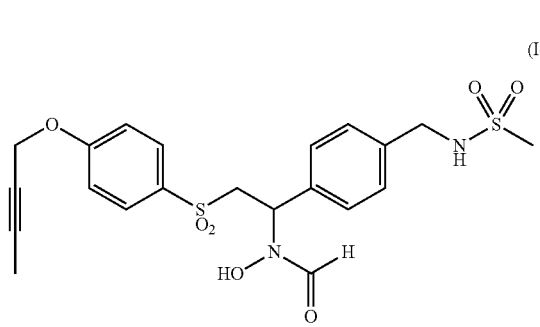

(I-4)

According to the same operation as in Example 3, the above-mentioned compound (I-4) was obtained.

MS (FAB) m/z: 481 (M+H)$^+$.

$^1$H-NMR (CDCl$_3$): δ 8.42 (0.6H, s), 7.87 (0.4H, s), 7.78-7.88 (2H, m), 7.30-7.35 (4H, m), 7.06-7.17 (2H, m), 5.65 (0.6H, m), 5.39 (0.4H, m), 4.75 (2H, m), 4.28 (2H, m), 4.15 (0.4H, m), 4.00 (0.6H, br t, J=12 Hz), 3.45 (1H, m), 2.91 (1.2H, s), 2.89 (1.8H, s), 1.87 (3H, m).

Example 5

N-{4-[2-(4-But-2-ynyloxybenzenesulfonyl)-1-(formylhydroxyamino)ethyl]benzyl}benzamide (I-5)

[Chemical Formula 11]

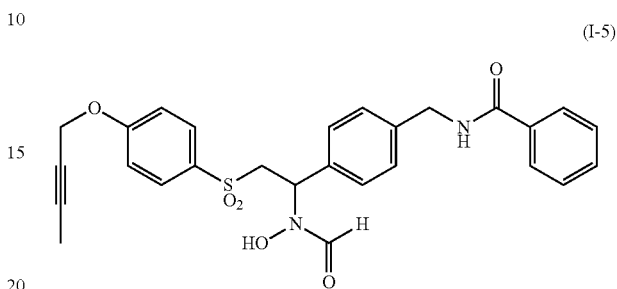

(I-5)

According to the same operation as in Example 3, the above-mentioned compound (I-5) was obtained.

MS (FAB) m/z: 507 (M+H)$^+$.

$^1$H-NMR (CDCl$_3$): δ 8.31 (0.6H, s), 8.08 (0.4H, s), 7.73-7.87 (4H, m), 7.51 (1H, m), 7.42 (2H m), 7.27-7.33 (3H, m), 7.07-7.14 (2H, m), 5.65 (0.6H, m), 5.37 (0.4H, m), 4.73 (2H, m), 4.54-4.62 (2H, m), 4.15 (0.4H, m), 4.00 (0.6H, m), 3.45 (1H, m), 1.86 (3H, br s).

Example 6

N-[2-(4-But-2-ynyloxybenzenesulfonyl)-1-(4-morpholin-4-ylmethylphenyl)ethyl]-N-hydroxyformamide (I-6)

[Chemical Formula 12]

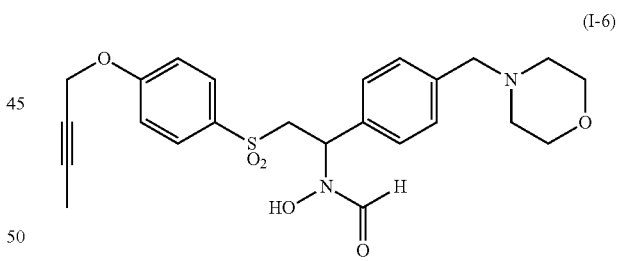

(I-6)

(6-1): tert-Butyl-(4-methanesulfonylphenoxy)dimethylsilane (XII-6)

9.9 g (145.18 mmol) of imidazole was added to and dissolved in an N,N-dimethylformamide solution (150 mL) of 10 g (58.07 mmol) of 4-methylsulfonylphenol, and then 10.5 g (69.7 mmol) of tert-butyldimethylchlorosilane was added thereto and stirred. After the reaction, brine was added thereto and extracted with ethyl acetate. The organic layer was washed three times with brine, and dried over anhydrous magnesium sulfate. Purifying by silica gel column chromatography (hexane/ethyl acetate=5/1→3/1) gave 15.97 g (55.75 mmol) of tert-butyl-(4-methanesulfonylphenoxy)dimethylsilane (XII-6) (yield 96%). Its physical properties are shown below.

¹H-NMR (CDCl₃): δ 7.83 (1H, m), 7.81 (1H, m), 6.97 (1H, m), 6.95 (1H, m), 3.04 (1H, s), 1.56 (9H, s), 0.25 (6H, s).

(6-2): 2-[4-(tert-Butyldimethylsilanyloxy)benzene-sulfonyl]-1-(4-morpholin-4-ylmethylphenyl)etha-none (XIII-6)

In an argon atmosphere at −78° C., 4.19 mL (8.37 mmol) of a hexane-heptane-ethylbenzene solution of 2.0 M lithium diisopropylamide was added to a tetrahydrofuran solution of 2.6 g (6.98 mmol) of tert-butyl-(4-methanesulfonylphenoxy)dimethylsilane (XII-6) obtained in the above (6-1), and 6.98 mL (6.98 mmol) of a tetrahydrofuran solution of 1.0 M lithium hexamethyldisilazide and 5 mL of a tetrahydrofuran solution of 1.6 g (6.98 mmol) of methyl 4-morpholin-4-ylm-ethylbenzoate (IX-6) were added thereto. Subsequently, this was gradually heated up to room temperature with stirring. After the reaction, brine was added thereto, extracted with ethyl acetate, and the organic layer was washed with brine. After dried over anhydrous magnesium sulfate, the solvent was evaporated away under reduced pressure. 3.74 g of 2-[4-(tert-butyldimethylsilanyloxy)benzenesulfonyl]-1-(4-mor-pholin-4-ylmethylphenyl)ethanone (XIII-6) was obtained as a roughly-purified product.

(6-3): 2-[4-(tert-Butyldimethylsilanyloxy)benzene-sulfonyl]-1-(4-morpholin-4-ylmethylphenyl)ethanol (XIV-6)

At 0° C., 264 mg (6.98 mmol) of sodium borohydride was added to a methanol (50 mL) solution of 3.74 g (6.98 mmol) of the compound (XIII-6) obtained in the above (6-2). After stirred for 1 hour, brine was added thereto. Methanol was evaporated away under reduced pressure, and the residue was extracted with ethyl acetate. The organic layer was washed with brine, and dried over anhydrous magnesium sulfate. The solvent was evaporated away under reduced pressure, and the residue was purified by silica gel column chromatography (ethyl acetate→ethyl acetate/methanol=10/1) to give 2.19 g (4.48 mmol) of 2-[4-(tert-butyldimethylsilanyloxy)benzene-sulfonyl]-1-(4-morpholin-4-ylmethylphenyl) ethanol (XIV-6). Its physical properties are shown below.

¹H-NMR (CDCl₃): δ 7.83 (2H, m), 7.25-7.30 (4H, m), 6.98 (2H, m), 5.22 (1H, d, J=7.7 Hz), 3.68 (4H, m), 3.46 (3H, m), 3.30 (1H, dd, J=1.5, 14 Hz), 2.40 (4H, m), 0.99 (9H, s), 0.25 (6H, s).

(6-4): 4-[(E)-2-(4-Morpholin-4-ylmethylphenyl)ethe-nesulfonyl]phenol (XVI-6)

3.10 mL of triethylamine was added to a dichloromethane solution (45 mL) of 2.19 g (4.48 mmol) of 2-[4-(tert-bu-tyldimethylsilanyloxy)benzenesulfonyl]-1-(4-morpholin-4-ylmethylphenyl)ethanol (XIV-6) obtained in the above (6-3), and stirred at 0° C. 0.61 mL (8.91 mmol) of methanesulfonyl chloride was added thereto, and stirred at room temperature for 8 hours. Further, 3.10 mL of triethylamine and 0.61 mL of methanesulfonyl chloride were added thereto, and stirred for 4 hours. Brine was added and extracted with chloroform. The organic layer was washed with brine, and dried over anhy-drous magnesium sulfate. The solvent was evaporated away under reduced pressure, and the residue was purified by silica gel column chromatography (hexane/ethyl acetate=1/2→ethyl acetate→ethyl acetate/methanol=10/1) to give 0.757 g (2.11 mmol) of 4-[(E)-2-(4-morpholin-4-ylmeth-ylphenyl)ethenesulfonyl]phenol (XVI-6) (yield 47%). Its physical properties are shown below.

¹H-NMR (CDCl₃): δ 8.01 (1H, d, J=8.7 Hz), 7.81 (1H, d, J=8.7 Hz), 7.61 (1H, d, J=15 Hz), 7.35-7.47 (5H, m), 6.92 (1H, d, J=6.9 Hz), 6.81 (1H, d, J=15 Hz), 3.71 (4H, m), 3.51 (2H, m), 2.44 (4H, m).

(6-5): 4-[4-[(E)-2-(4-But-2-ynyloxybenzenesulfonyl)vinyl]benzyl]morpholine (II-6)

108 mg (0.780 mmol) of potassium carbonate and 0.094 mL (1.04 mmol) of 1-bromo-2-butyne were added to an N,N-dimethylformamide solution of 187 mg (0.520 mmol) of 4-[(E)-2-(4-morpholin-4-ylmethylphenyl)ethenesulfonyl]phenol (XVI-6) obtained in the above (6-4), and stirred for 4 hours. Brine was added thereto, and extracted with ethyl acetate. The organic layer was washed with brine, and dried over anhydrous magnesium sulfate. The solvent was evaporated away under reduced pressure, and the residue was purified by silica gel column chromatography (ethyl acetate/chloroform=1/1→1/2→ethyl acetate) to give 0.0238 g (0.0578 mmol) of 4-[4-[(E)-2-(4-but-2-ynyloxybenzenesulfonyl)vinyl]benzyl]morpholine (II-6) (yield 11%). Its physical properties are shown below.

¹H-NMR (CDCl₃): δ 7.87 (2H, d, J=8.7 Hz), 7.63 (1H, d, J=15.5 Hz), 7.35-7.44 (4H, m), 7.07 (2H, d, J=8.7 Hz), 6.83 (1H, d, J=15.5 Hz), 4.71 (2H, m), 3.69 (4H, m), 3.50 (2H, s), 2.43 (4H, m), 1.86 (3H, s).

(6-6): N-[2-(4-But-2-ynyloxybenzenesulfonyl)-1-(4-morpholin-4-ylmethylphenyl)ethyl]-N-hydroxyfor-mamide (I-6)

According to the same process as in the above (1-7 and 1-8) but using the compound (II-6) obtained in the above (6-5), N-[2-(4-but-2-ynyloxybenzenesulfonyl)-1-(4-morpholin-4-ylmethylphenyl)ethyl]-N-hydroxyformamide (I-6) was obtained. Its physical properties are shown below.

MS (FAB) m/z: 473 (M+H)⁺.

¹H-NMR (CDCl₃): δ 8.45 (0.6H, s), 8.11 (0.4H, s), 7.80-7.88 (2H, m), 7.23-7.32 (4H, m), 7.07-7.16 (2H, m), 5.63 (0.6H, m), 5.38 (0.4H, m), 4.75 (2H, m), 4.19 (0.4H, m), 4.03 (0.6H, m), 3.64-3.71 (4H, m), 3.40-3.51 (2H, m), 2.39 (4H, m), 1.87 (3H, m).

Example 7

N-Hydroxy-N-[1-(4-morpholin-4-ylmethylphenyl)-2-(4-pent-2-ynyloxybenzenesulfonyl)ethyl]forma-mide (I-7)

[Chemical Formula 13]

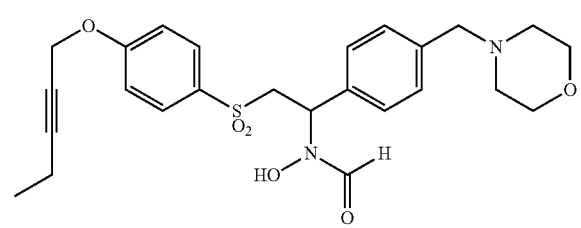

(I-7)

According to the same operation as in Example 6, the above-mentioned compound (I-7) was obtained.

MS (FAB) m/z: 487 (M+H)+.

$^1$H-NMR (CDCl$_3$): δ 8.44 (0.6H, s), 8.11 (0.4H, s), 7.78-7.88 (2H, m), 7.26-7.32 (4H, m), 7.06-7.16 (2H, m), 5.63 (0.6H, dd, J=3.6, 12.3 Hz), 5.38 (0.4H, dd, J=3.0, 10.1 Hz), 4.75 (2H, m), 4.18 (0.4H, dd, J=10.1, 15.7 Hz), 4.03 (0.6H, dd, J=12.3, 14.6 Hz), 3.72 (2H, q, J=6.9 Hz), 3.64-3.70 (4H, m), 3.41-3.48 (3H, m), 2.36-2.43 (4H, m), 1.24 (3H, t, J=6.9 Hz).

According to the schemes 1 to 4 and according to the same process as in Examples 1 to 7, the following compounds (I-8 to I-28) were obtained.

Example 8

N-[2-(4-But-2-ynyloxybenzenesulfonyl)-1-(4-dimethylaminophenyl)ethyl]-N-hydroxyformamide (I-8)

[Chemical Formula 14]

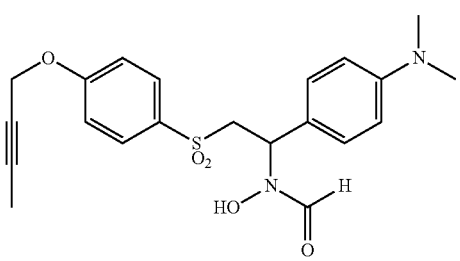

(I-8)

MS (ESI) m/z: 417 (M+H)+.

$^1$H-NMR (CDCl$_3$): δ 8.40 (0.5H, s), 8.04 (0.5H, s), 7.73-7.89 (2H, m), 7.02-7.22 (4H, m), 6.62 (2H, d, J=8.7 Hz), 5.49-5.58 (0.5H, m), 5.22-5.31 (0.5H, m), 4.73 (2H, d, J=9.2 Hz), 3.98-4.23 (1H, m), 3.37-3.55 (1H, m), 2.93 (3H, s), 2.91 (3H, s), 1.87 (3H, t, J=2.3 Hz).

Example 9

N-[2-(4-But-2-ynyloxybenzenesulfonyl)-1-(3-dimethylaminophenyl)ethyl]-N-hydroxyformamide (I-9)

[Chemical Formula 15]

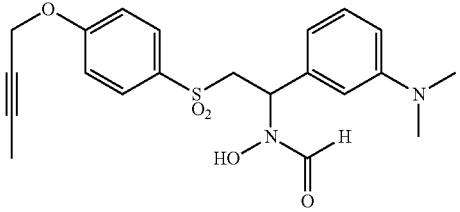

(I-9)

MS (ESI) m/z: 417 (M+H)+.

$^1$H-NMR (CDCl$_3$): δ 8.45 (0.5H, s), 8.07 (0.5H, s), 7.77-7.89 (2H, m), 7.04-7.21 (4H, m), 6.57-6.68 (2H, m), 5.54-5.62 (0.5H, m), 5.27-5.34 (0.5H, m), 4.69-4.77 (2H, m), 4.00-4.25 (1H, m), 3.41-3.54 (1H, m), 2.90-2.95 (6H, m), 1.87 (3H, t, J=2.3 Hz).

Example 10

N-[2-(4-But-2-ynyloxybenzenesulfonyl)-1-(2-dimethylaminophenyl)ethyl]-N-hydroxyformamide (I-10)

[Chemical Formula 16]

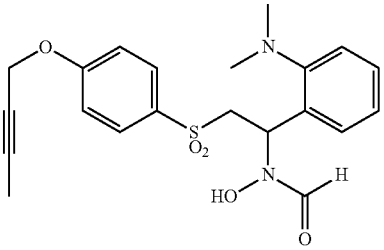

(I-10)

MS (ESI) m/z: 417 (M+H)+.

$^1$H-NMR (CDCl$_3$): δ 8.31 (0.6H, s), 8.08 (0.4H, s), 7.88 (0.6H, d, J=9.2 Hz), 7.83 (0.4H, d, J=8.7 Hz), 7.07-7.42 (6H, m), 6.57-6.68 (2H, m), 6.04 (0.4H, dd, J=2.7, 10 Hz), 5.88 (0.6H, dd, J=2.7, 11 Hz), 4.71-4.78 (2H, m), 3.99-4.08 (1H, m), 3.39-3.51 (1H, m), 2.61 (2.4H, s), 2.54 (3.6H, s), 1.86 (3H, t, J=2.3 Hz).

Example 11

N-[2-(4-But-2-ynyloxybenzenesulfonyl)-1-(4-piperidin-1-ylmethylphenyl)ethyl]-N-hydroxyformamide (I-11)

[Chemical Formula 17]

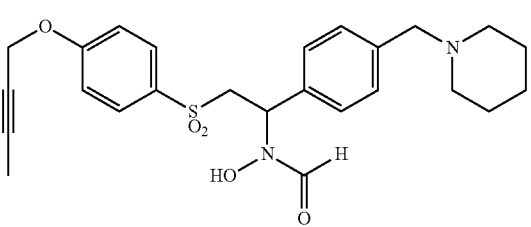

(I-11)

MS (ESI) m/z: 471 (M+H)+.

$^1$H-NMR (CDCl$_3$): δ 8.28 (0.6H, s), 8.10 (0.4H, s), 7.77-7.89 (2H, m), 7.04-7.30 (6H, m), 5.61-5.69 (0.6H, m), 5.315.39 (0.4H, m), 4.69-4.78 (2H, m), 3.99-4.26 (1H, m), 3.35-3.53 (3H, m), 2.37 (4H, br s), 1.87 (3H, br s), 1.35-1.59 (6H, m).

Example 12

N-[2-(4-But-2-ynyloxybenzenesulfonyl)-1-(3-piperidin-1-ylmethylphenyl)ethyl]hydroxyformamide (I-12)

[Chemical Formula 18]

Example 14

N-[2-(4-But-2-ynyloxybenzenesulfonyl)-1-{4-[(ethylmethylamino)methyl]phenyl]ethyl}-N-hydroxyformamide (I-14)

[Chemical Formula 20]

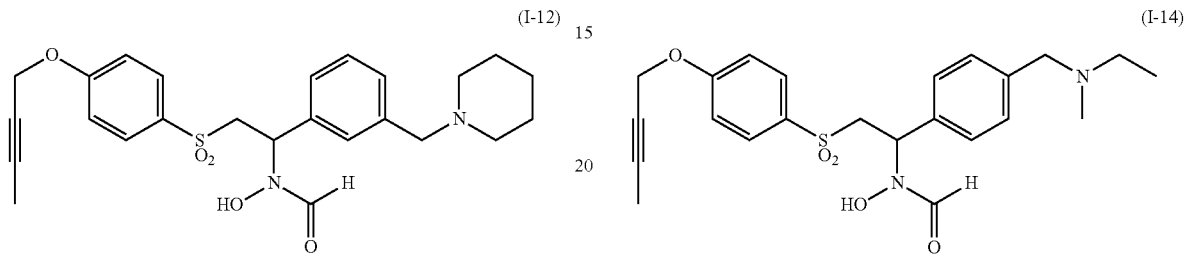

MS (ESI) m/z: 471 (M+H)$^+$.

$^1$H-NMR (CDCl$_3$): δ 8.38 (0.5H, s), 8.10 (0.5H, s), 7.77-7.89 (2H, m), 7.04-7.30 (6H, m), 5.70 (0.5H, dd, J=3.7, 11 Hz), 5.30-5.38 (0.5H, m), 4.69-4.77 (2H, m), 4.01-4.27 (1H, m), 3.23-3.60 (3H, m), 2.30 (4H, br s), 1.87 (3H, t, J=2.3 Hz), 1.31-1.55 (6H, m).

MS (ESI) m/z: 445 (M+H)$^+$.

$^1$H-NMR (CDCl$_3$): δ 8.35 (0.5H, s), 8.11 (0.5H, s), 7.78-7.89 (2H, m), 7.06-7.28 (6H, m), 5.65 (0.5H, dd, J=3.7, 12 Hz), 5.32-5.40 (0.5H, m), 4.71-4.77 (2H, m), 3.99-4.24 (1H, m), 3.38-3.53 (3H, m), 2.38 (3H, q, J=7.3 Hz), 1.87 (3H, t, J=2.3 Hz), 1.05 (3H, t, J=7.3 Hz).

Example 13

N-[2-(4-But-2-ynyloxybenzenesulfonyl)-1-(3-morpholin-4-ylmethylphenyl)ethyl]-N-hydroxyformamide (I-13)

[Chemical Formula 19]

Example 15

N-(2-(4-But-2-ynyloxybenzenesulfonyl)-1-{3-[(ethylmethylamino)methyl]phenyl}ethyl)-N-hydroxyformamide (I-15)

[Chemical Formula 21]

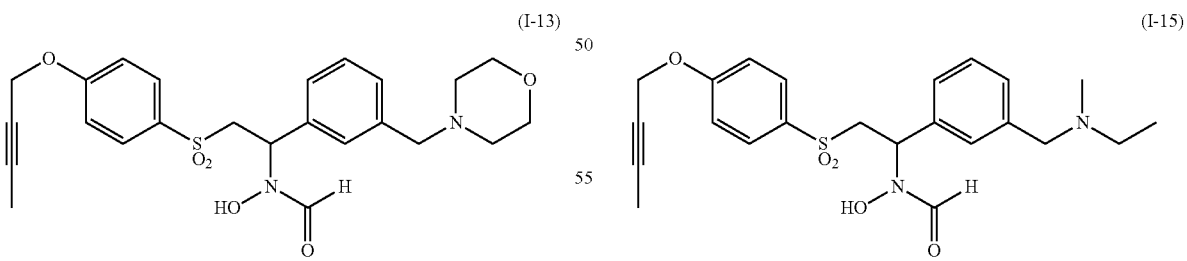

MS (ESI) m/z: 473 (M+H)$^+$.

$^1$H-NMR (CDCl$_3$): δ 8.46 (0.5H, s), 8.10 (0.5H, s), 7.78-7.90 (2H, m), 7.06-7.31 (6H, m), 5.65 (0.5H, dd, J=3.7, 12 Hz), 5.35-5.42 (0.5H, m), 4.70-4.78 (2H, m), 3.98-4.26 (1H, m), 3.68 (4H, dd, J=4.6, 4.6 Hz), 3.39-3.54 (3H, m), 2.36-2.44 (4H, m), 1.87 (3H, t, J=2.3 Hz).

MS (ESI) m/z: 445 (M+H)$^+$.

$^1$H-NMR (CDCl$_3$): δ 8.37 (0.5H, s), 8.11 (0.5H, s), 7.78-7.90 (2H, m), 7.06-7.34 (6H, m), 5.70 (0.5H, dd, J=3.7, 12 Hz), 5.32-5.40 (0.5H, m), 4.70-4.78 (2H, m), 4.00-4.22 (1H, m), 3.29-3.59 (3H, m), 2.38 (3H, q, J=6.9 Hz), 1.87 (3H, t, J=2.3 Hz), 1.03 (3H, t, J=6.9 Hz).

Example 16

N-{4-[2-(4-But-2-ynyloxybenzenesulfonyl)-1-(formylhydroxyamino)ethyl]benzyl}-N-methyl-methanesulfonamide (I-16)

[Chemical Formula 22]

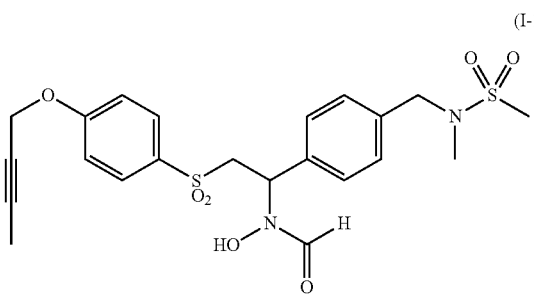

(I-16)

MS (ESI) m/z: 495 (M+H)$^+$.

$^1$H-NMR (DMSO-d$_6$): δ 8.22 (0.5H, br s), 8.11 (0.5H, br s), 7.75-7.86 (2H, m), 7.09-7.42 (4H, m), 7.13 (2H, d, J=9.2 Hz), 5.70 (0.5H, br s), 5.40 (0.5H, br s), 4.83-4.89 (2H, m), 4.18 (2H, s), 3.86-4.16 (2H, m), 2.94 (3H, s), 2.63 (3H, s), 1.84 (3H, t, J=2.3 Hz).

Example 17

N-{4-[2-(4-But-2-ynyloxybenzenesulfonyl)-1-(formylhydroxyamino)ethyl]benzyl}-N-methylbenzenesulfonamide (I-17)

[Chemical Formula 23]

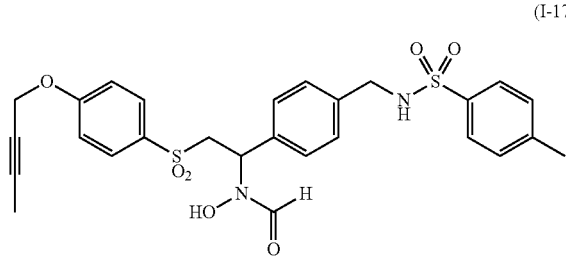

(I-17)

MS (ESI) m/z: 557 (M+H)$^+$.

$^1$H-NMR (CDCl$_3$): δ 8.37 (0.6H, br s), 8.03 (0.4H, br s), 7.69-7.88 (4H, m), 7.04-7.33 (8H, m), 5.61 (0.6H, dd, J=3.6, 12 Hz), 5.31-5.39 (0.4H, m), 4.70-4.83 (2H, m), 3.92-4.17 (3H, m), 3.36-3.51 (1H, m), 2.43 (3H, s), 1.87 (3H, t, J=2.3 Hz).

Example 18

N-{4-[2-(4-But-2-ynyloxybenzenesulfonyl)-1-(formylhydroxyamino)ethyl]benzyl}-4,N-dimethyl-benzenesulfonamide (I-18)

[Chemical Formula 24]

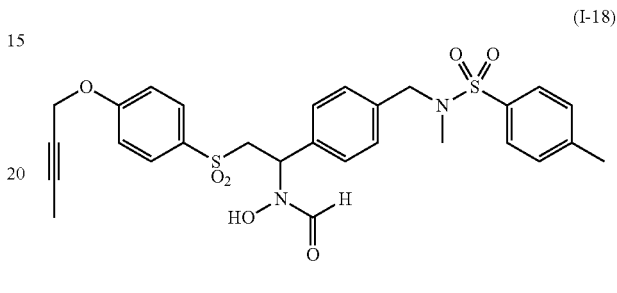

(I-18)

MS (ESI) m/z: 571 (M+H)$^+$.

$^1$H-NMR (CDCl$_3$): δ 8.47 (0.6H, br s), 8.11 (0.4H, br s), 7.78-7.89 (2H, m), 7.70 (2H, d, J=8.2 Hz), 7.35 (2H, d, J=8.2 Hz), 7.23-7.32 (4H, m), 7.06-7.17 (2H, m), 5.64 (0.6H, dd, J=3.6, 12 Hz), 5.36-5.43 (0.4H, m), 4.71-4.78 (2H, m), 3.96-4.22 (3H, m), 3.38-3.52 (1H, m), 2.58 (1.2H, s), 2.54 (1.8H, s), 2.45 (3H, s), 1.87 (3H, t, J=2.3 Hz).

Example 19

N-{4-[2-(4-But-2-ynyloxybenzenesulfonyl)-1-(formylhydroxyamino)ethyl]benzyl}-N-methylsulfonylmethanesulfonamide (I-19)

[Chemical Formula 25]

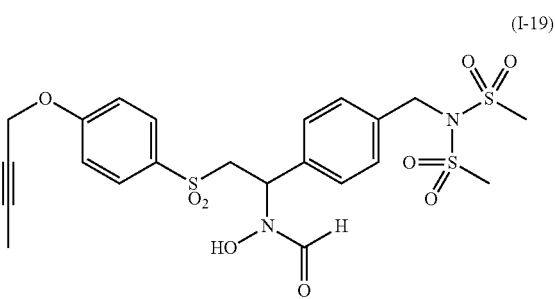

(I-19)

MS (ESI) m/z: 559 (M+H)$^+$.

$^1$H-NMR (DMSO-d$_6$): δ 8.12 (0.5H, br s), 8.21 (0.5H, br s), 7.80 (2H, br s), 7.35-7.44 (1H, m), 7.32 (2H, d, J=9.2 Hz), 7.31 (1H, s), 7.14 (2H, d, J=9.2 Hz), 5.41 (0.5H, br s), 5.71 (0.5H, br s), 4.87 (2H, q, J=2.3 Hz), 4.83 (2H, s), 4.00-4.16 (1H, m), 3.84-3.98 (1H, m), 3.25 (6H, s), 1.84 (3H, t, J=2.3 Hz).

Example 20

N-{2-(4-But-2-ynyloxybenzenesulfonyl)-1-[4-(2-dimethylaminoethyl)phenyl]ethyl}-N-hydroxyformamide (I-20)

[Chemical Formula 26]

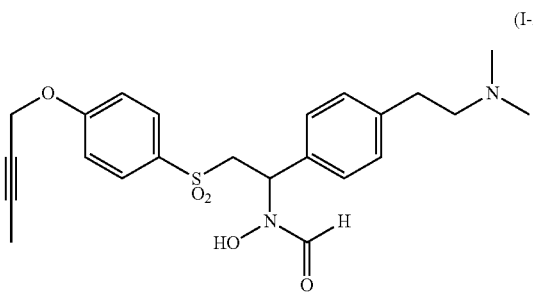

(I-20)

MS (ESI) m/z: 445 (M+H)$^+$.

$^1$H-NMR (CDCl$_3$): δ 8.30 (0.5H, s), 8.14 (0.5H, s), 7.76-7.89 (2H, m), 7.00-7.24 (6H, m), 5.71 (0.5H, dd, J=3.7, 11 Hz), 5.29-5.36 (0.5H, m), 4.69-4.76 (2H, m), 4.02-4.21 (1H, m), 3.42-3.59 (1H, m), 2.43-2.54 (2H, m), 2.10-2.28 (2H, m), 2.19 (6H, s), 1.87 (3H, t, J=2.3 Hz).

Example 21

N-{2-(4-But-2-ynyloxybenzenesulfonyl)-1-[4-(2-morpholin-4-ylethyl)phenyl]ethyl}-N-hydroxyformamide (I-21)

[Chemical Formula 27]

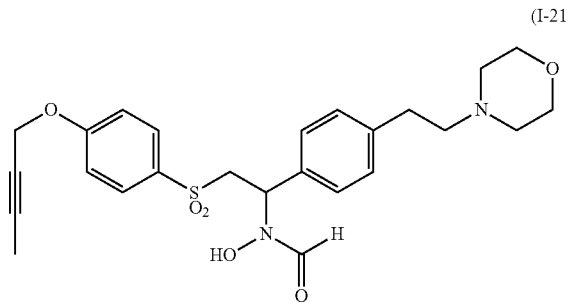

(I-21)

MS (ESI) m/z: 487 (M+H)$^+$.

$^1$H-NMR (CDCl$_3$): δ 8.44 (0.5H, s), 8.10 (0.5H, s), 7.77-7.89 (2H, m), 7.05-7.27 (6H, m), 5.62 (0.5H, dd, J=3.7, 12 Hz), 5.32-5.39 (0.5H, m), 4.69-4.78 (2H, m), 3.96-4.23 (1H, m), 3.71 (4H, dd, J=4.1, 4.6 Hz), 3.39-3.53 (1H, m), 2.69-2.77 (2H, m), 2.43-2.56 (6H, m), 1.87 (3H, t, J=2.3 Hz).

Example 22

N-(2-{4-[2-(4-But-2-ynyloxybenzenesulfonyl)-1-(formylhydroxyamino)ethyl]phenyl}ethyl)methanesulfonamide (I-22)

[Chemical Formula 28]

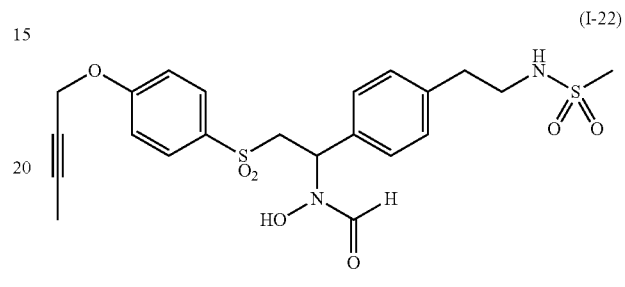

(I-22)

MS (ESI) m/z: 495 (M+H)$^+$.

$^1$H-NMR (CDCl$_3$): δ 8.39 (0.5H, s), 8.07 (0.5H, s), 7.78-7.89 (2H, m), 7.05-7.30 (6H, m), 5.65 (0.5H, dd, J=3.7, 12 Hz), 5.33-5.41 (0.5H, m), 4.70-4.78 (2H, m), 3.95-4.21 (1H, m), 3.31-3.52 (3H, m), 2.80-2.91 (5H, m), 1.87 (3H, t, J=2.3 Hz).

Example 23

N-{2-(4-But-2-ynyloxybenzenesulfonyl)-1-[4-(3-dimethylaminopropyl)phenyl]ethyl}-N-hydroxyformamide (I-23)

[Chemical Formula 29]

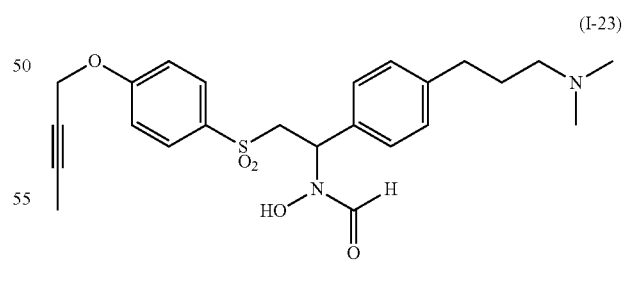

(I-23)

MS (ESI) m/z: 459 (M+H)$^+$.

$^1$H-NMR (CDCl$_3$): δ 8.06-8.13 (1H, m), 7.74-7.88 (2H, m), 7.02-7.24 (6H, m), 5.64-5.75 (0.5H, m), 5.22-5.32 (0.5H, m), 4.68-4.76 (2H, m), 4.02-4.22 (1H, m), 3.40-3.58 (1H, m), 2.51 (2H, dd, J=7.3, 7.8 Hz), 2.17 (2H, dd, J=7.3, 7.8 Hz), 2.08 (3H, s), 2.06 (3H, s), 1.87 (3H, t, J=2.3 Hz), 1.52-1.66 (2H, m).

Example 24

N-{2-(4-But-2-ynyloxybenzenesulfonyl)-1-[4-(3-diethylaminopropyl)phenyl]ethyl}-N-hydroxyformamide (I-24)

[Chemical Formula 30]

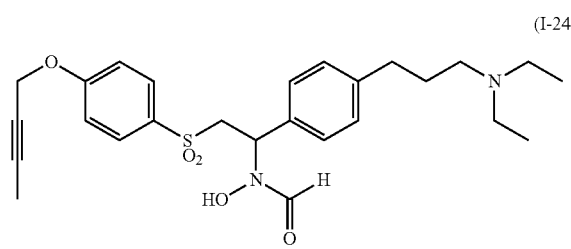

(I-24)

MS (ESI) m/z: 487 (M+H)$^+$.

$^1$H-NMR (CDCl$_3$): δ 8.29 (0.5H, s), 8.07 (0.5H, m), 7.75-7.89 (2H, m), 7.04-7.24 (6H, m), 5.64 (0.5H, dd, J=3.7, 11 Hz), 5.28-5.37 (0.5H, m), 4.69-4.77 (2H, m), 4.00-4.23 (1H, m), 3.41-3.55 (1H, m), 2.33-2.60 (6H, m), 1.87 (3H, t, J=2.3 Hz), 1.61-1.72 (2H, m), 0.91-1.01 (6H, m).

Example 25

N-{2-(4-But-2-ynyloxybenzenesulfonyl)-1-[4-(3-morpholin-4-ylpropyl)phenyl]ethyl}-N-hydroxyformamide (I-25)

[Chemical Formula 31]

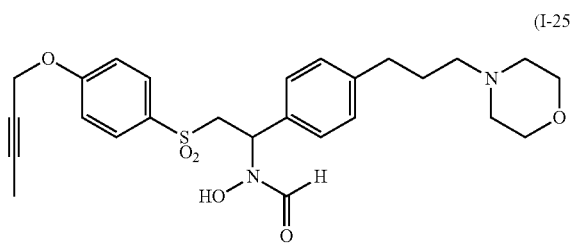

(I-25)

MS (ESI) m/z: 501 (M+H)$^+$.

$^1$H-NMR (CDCl$_3$): δ 8.37 (0.5H, s), 8.08 (0.5H, s), 7.76-7.89 (2H, m), 7.04-7.24 (6H, m), 5.64 (0.5H, dd, J=3.7, 12 Hz), 5.29-5.38 (0.5H, m), 4.68-4.77 (2H, m), 3.98-4.23 (1H, m), 3.67 (4H, br s), 3.40-3.53 (1H, m), 2.52-2.63 (2H, m), 2.24-2.46 (6H, m), 1.87 (3H, t, J=2.3 Hz), 1.65-1.76 (2H, m).

Example 26

N-{2-(4-But-2-ynyloxybenzenesulfonyl)-1-[4-(4-morpholin-4-ylbutyl)phenyl]ethyl}-N-hydroxyformamide (I-26)

[Chemical Formula 32]

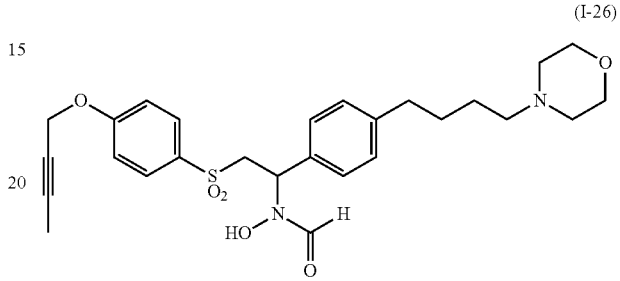

(I-26)

MS (ESI) m/z: 515 (M+H)$^+$.

$^1$H-NMR (CDCl$_3$): δ 8.41 (0.5H, s), 8.10 (0.5H, s), 7.77-7.89 (2H, m), 7.05-7.24 (6H, m), 5.57-5.66 (0.5H, m), 5.31-5.38 (0.5H, m), 4.69-4.77 (2H, m), 3.97-4.23 (1H, m), 3.67 (4H, dd, J=4.1, 4.6 Hz), 3.40-3.53 (1H, m), 2.52-2.63 (2H, m), 2.24-2.46 (6H, m), 1.87 (3H, t, J=2.3 Hz), 1.39-1.63 (4H, m).

Example 27

N-{4-[1-(Formylhydroxyamino)-2-(4-pent-2-ynyloxybenzenesulfonyl)ethyl]benzyl}methanesulfonamide (I-27)

[Chemical Formula 33]

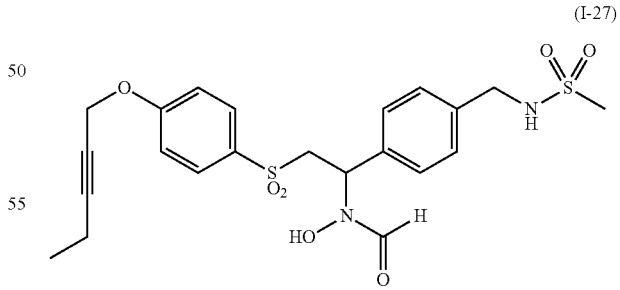

(I-27)

MS (ESI) m/z: 495 (M+H)$^+$.

$^1$H-NMR (CDCl$_3$): δ 8.29 (0.6H, s), 8.00 (0.4H, s), 7.75-7.88 (2H, m), 7.23-7.35 (4H, m), 7.05-7.16 (2H, m), 5.66 (0.6H, dd, J=3.7, 12 Hz), 5.31-5.41 (0.4H, m), 4.71-4.80 (2H, m), 4.26 (2H, br s), 3.95-4.18 (1H, m), 3.39-3.50 (1H, m), 2.89 (3H, br s), 2.24 (2H, tq, J=1.8, 7.3 Hz), 1.14 (3H, t, J=7.3 Hz).

Example 28

N-{4-[1-(Formylhydroxyamino)-2-(4-oct-2-ynyloxy-benzenesulfonyl)ethyl]benzyl}methanesulfonamide
(I-28)

[Chemical Formula 34]

(I-28)

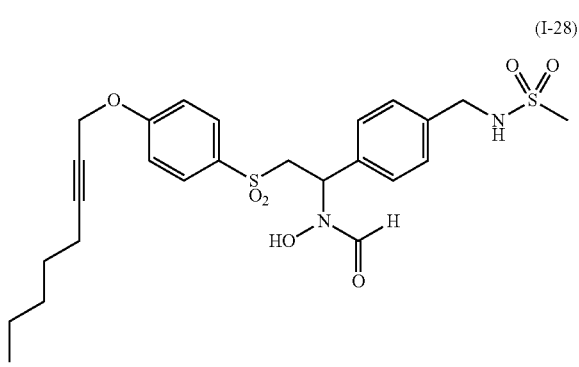

MS (ESI) m/z: 537 (M+H)$^+$.
$^1$H-NMR (CDCl$_3$): δ 8.35 (0.6H, s), 8.03 (0.4H, s), 7.76-7.88 (2H, m), 7.27-7.36 (4H, m), 7.06-7.17 (2H, m), 5.66 (0.6H, dd, J=3.7, 12 Hz), 5.34-5.42 (0.4H, m), 4.72-4.82 (2H, m), 4.23-4.33 (2H, m), 3.94-4.18 (1H, m), 3.38-3.51 (1H, m), 2.90 (1.2H, s), 2.89 (1.8H, s), 2.22 (2H, tt, J=2.3, 7.3 Hz), 1.45-1.55 (2H, m), 1.23-1.38 (4H, m), 0.87 (3H, t, J=7.3 Hz).

Test Example 1

ADAM17 Inhibition Test

The nucleotide sequence of ADAM17 was reported by Moss et al. (Moss, M. L. et al., Nature 1997, 385, 733-736). Accordingly, the cDNA was obtained from THP-1 cells of a human monocytic cell line in the usual way, and this was inserted into an expression vector, and thereafter the vector was transformed in mammal cells or insect cells to thereby make the cells express ADAM17.

In the ADAM17 inhibition test, ADAM17 obtained in the manner as above was used as an enzyme, and a fluorescent synthetic substrate Nma (N-methylanthranylic acid)-Leu-Ala-Gln-Ala-Val-Arg-Ser-Ser-Lys-Dnp (dinitrophenyl)-D-Arg-NH$_2$ containing the ADAM17-cleaved sequence of a membrane-bound TNF was used as the substrate. Using these in the test, the ADAM17 activity in the presence or absence of the test substance was measured. The method of ADAM17 inhibition test is mentioned below.

Concretely, 90 μl of an enzyme liquid as prepared to have 14 units in an assay buffer A (50 mM tris-hydrochloride buffer (pH 7.5) containing 200 mM sodium chloride, 5 mM calcium chloride, 10 μM zinc sulfate, 0.004% sodium azide, and 2 mg/mL bovine serum albumin) (the amount of enzyme capable of decomposing 1 pmol of substrate at 25° C. for 1 minute was defined to be 1 unit), and 90 μL a fluorescent synthetic substrate as prepared to be 20 μM in an assay buffer B (50 mM tris-hydrochloride buffer (pH 7.5) containing 200 mM sodium chloride, 5 mM calcium chloride, 10 μM zinc sulfate, 0.004% sodium azide, and 0.05% PLURONIC F-68) were mixed, and reacted at 37° C. for 1.5 hours. Subsequently, using a fluorescent intensity meter (Fluoroskan Ascent), the reaction liquid was analyzed at an excitation wavelength of 355 nm and at a measuring wavelength of 460 nm to determine the enzymatic activity therein.

From the enzymatic activity in the presence or absence of the test compound, the inhibitory percentage was determined, and the 50% inhibitory concentration (IC$_{50}$) of the test compound was calculated.

The 50% inhibitory concentration against ADAM17 of the N-hydroxyformamide derivative of the invention, as determined in this test, was shown in Table 1.

TABLE 1

| Compound | IC$_{50}$ Value (nM) |
|---|---|
| I-1 | 5.2 |
| I-2 | 7.2 |
| I-3 | 8.2 |
| I-4 | 5.8 |
| I-5 | 7.2 |
| I-6 | 18 |
| I-7 | 55 |

Test Example 2

ADAM10 Inhibition Test

The cDNA of ADAM10 was obtained from THP-1 cells in the usual way, and this was inserted into an expression vector, and thereafter the vector was transformed in mammal cells or insect cells to thereby make the cells express ADAM10. In the ADAM10 inhibition test, ADAM10 obtained in the manner as above was used as an enzyme, and a fluorescent synthetic substrate Nma (N-methylanthranylic acid)-Leu-Ala-Gln-Ala-Val-Arg-Ser-Ser-Lys-Dnp (dinitrophenyl)-D-Arg-NH$_2$ was used as the substrate. Using these in the test, the ADAM10 activity in the presence or absence of the test substance was measured. The method of ADAM10 inhibition test is mentioned below.

Concretely, 90 μl of an enzyme liquid prepared using an assay buffer A (50 mM tris-hydrochloride buffer (pH 7.5) containing 200 mM sodium chloride, 5 mM calcium chloride, 10 μM zinc sulfate, 0.004% sodium azide, and 2 mg/mL bovine serum albumin), and 90 μL a fluorescent synthetic substrate as prepared to be 20 μM in an assay buffer B (50 mM tris-hydrochloride buffer (pH 7.5) containing 200 mM sodium chloride, 5 mM calcium chloride, 10 μM zinc sulfate, 0.004% sodium azide, and 0.05% PLURONIC F-68) were mixed, and reacted at 25° C. for 5 hours. Subsequently, using a fluorescent intensity meter (Fluoroskan Ascent), the reaction liquid was analyzed at an excitation wavelength of 355 nm and at a measuring wavelength of 460 nm to determine the enzymatic activity therein.

From the enzymatic activity in the presence or absence of the test compound, the inhibitory percentage was determined, and the 50% inhibitory concentration (IC$_{50}$) of the test compound was calculated.

The 50% inhibitory concentration against ADAM10 of the N-hydroxyformamide derivative of the invention, as determined in this test, was shown in Table 2.

TABLE 2

| Compound | IC$_{50}$ Value (nM) |
|---|---|
| I-1 | 13 |
| I-2 | 22 |
| I-3 | 42 |
| I-4 | 40 |

TABLE 2-continued

| Compound | IC$_{50}$ Value (nM) |
|---|---|
| I-5 | 19 |
| I-6 | 70 |
| I-7 | 90 |

INDUSTRIAL APPLICABILITY

The N-hydroxyformamide derivative of the invention exhibits an excellent ADAM17 inhibitory activity and is useful as a medicament for treatment and prevention of ADAM17-related disorders. In addition, of the N-hydroxyformamide derivative of the invention, those having an ADAM17 inhibitory activity and additionally having an ADAM10 inhibitory activity are more useful as a medicament for treatment and prevention of disorders which both ADAM17 and ADAM10 are closely related.

The invention claimed is:

1. A compound represented by the following general formula (I), or a salt thereof, or a solvate thereof:

[Chemical Formula 1]

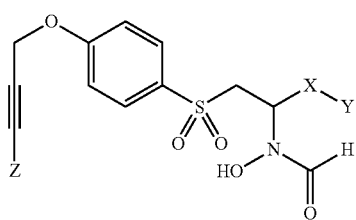

(I)

wherein X represents a phenylene group;
Y represents —(CH$_2$)$_m$R$^1$;
m indicates an integer of from 0 to 4;
R$^1$ represents:

[Chemical Formula 2]

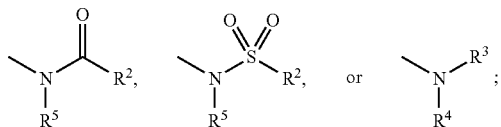

R$^2$ represents an optionally-substituted C1-C6 alkyl group, an optionally-substituted aryl group, or a C1-C6 alkoxy group;
R$^3$ and R$^4$ each independently represent a hydrogen atom, a C1-C6 alkyl group, or R$^3$ and R$^4$ may form a nitrogen-containing hetero ring along with the nitrogen atom adjacent thereto;
R$^5$ represents a hydrogen atom, a C1-C6 alkyl group or a C1-C6 alkylsulfonyl group;
Z represents a hydrogen atom or a C1-C6 alkyl group.

2. The compound or a salt thereof or a solvate thereof according to claim 1, wherein the compound represented by the general formula (I) is the following: N-[2-(4-but-2-ynyloxybenzenesulfonyl)-1-(4-diethylaminomethylphenyl)ethyl]-N-hydroxyformamide, N-[2-(4-but-2-ynyloxybenzenesulfonyl)-1-(4-dimethylaminomethylphenyl)ethyl]-N-hydroxyformamide, N-{4-[2-(4-but-2-ynyloxybenzenesulfonyl)-1-(formylhydroxyamino)ethyl]benzyl}-2-methoxyacetamide, N-{4-[2-(4-but-2-ynyloxybenzenesulfonyl)-1-(formylhydroxyamino)ethyl]benzyl}methanesulfonamide, N-{4-[2-(4-but-2-ynyloxybenzenesulfonyl)-1-(formylhydroxyamino)ethyl]benzyl}benzamide, N-[2-(4-but-2-ynyloxybenzenesulfonyl)-1-(4-morpholin-4-ylmethylphenyl)ethyl]-N-hydroxyformamide, N-hydroxy-N-[1-(4-morpholin-4-ylmethylphenyl)-2-(4-pent-2-ynyloxybenzenesulfonyl)ethyl]formamide, N-[2-(4-but-2-ynyloxybenzenesulfonyl)-1-(4-dimethylaminophenyl)ethyl]-N-hydroxyformamide, N-[2-(4-but-2-ynyloxybenzenesulfonyl)-1-(3-dimethylaminophenyl)ethyl]-N-hydroxyformamide, N-[2-(4-but-2-ynyloxybenzenesulfonyl)-1-(2-dimethylaminophenyl)ethyl]-N-hydroxyformamide, N-[2-(4-but-2-ynyloxybenzenesulfonyl)-1-(4-piperidin-1-ylmethylphenyl)ethyl]-N-hydroxyformamide, N-[2-(4-but-2-ynyloxybenzenesulfonyl)-1-(3-piperidin-1-ylmethylphenyl)ethyl]-N-hydroxyformamide, N-[2-(4-but-2-ynyloxybenzenesulfonyl)-1-(3-morpholin-4-ylmethylphenyl)ethyl]-N-hydroxyformamide, N-[2-(4-but-2-ynyloxybenzenesulfonyl)-1-{4-[(ethylmethylamino)methyl]phenyl}ethyl]-N-hydroxyformamide, N-(2-(4-but-2-ynyloxybenzenesulfonyl)-1-{3-[(ethylmethylamino)methyl]phenyl}ethyl)-N-hydroxyformamide, N-{4-[2-(4-but-2-ynyloxybenzenesulfonyl)-1-(formylhydroxyamino)ethyl]benzyl}-N-methylmethanesulfonamide, N-{4-[2-(4-but-2-ynyloxybenzenesulfonyl)-1-(formylhydroxyamino)ethyl]benzyl}-4-methylbenzenesulfonamide, N-{4-[2-(4-but-2-ynyloxybenzenesulfonyl)-1-(formylhydroxyamino)ethyl]benzyl}-4,N-dimethylbenzenesulfonamide, N-{4-[2-(4-but-2-ynyloxybenzenesulfonyl)-1-(formylhydroxyamino)ethyl]benzyl}-N-methylsulfonylmethanesulfonamide, N-{2-(4-but-2-ynyloxybenzenesulfonyl)-1-[4-(2-dimethylaminoethyl)phenyl]ethyl}-N-hydroxyformamide, N-{2-(4-but-2-ynyloxybenzenesulfonyl)-1-[4-(2-morpholin-4-ylethyl)phenyl]ethyl}-N-hydroxyformamide, N-(2-{4-[2-(4-but-2-ynyloxybenzenesulfonyl)-1-(formylhydroxyamino)ethyl]phenyl}ethyl)methanesulfonamide, N-{2-(4-but-2-ynyloxybenzenesulfonyl)-1-[4-(3-dimethylaminopropyl)phenyl]ethyl}-N-hydroxyformamide, N-{2-(4-but-2-ynyloxybenzenesulfonyl)-1-[4-(3-diethylaminopropyl)phenyl]ethyl}-N-hydroxyformamide, N-{2-(4-but-2-ynyloxybenzenesulfonyl)-1-[4-(3-morpholin-4-ylpropyl)phenyl]ethyl}-N-hydroxyformamide, N-{2-(4-but-2-ynyloxybenzenesulfonyl)-1-[4-(4-morpholin-4-ylbutyl)phenyl]ethyl}-N-hydroxyformamide, N-{4-[1-(formylhydroxyamino)-2-(4-pent-2-ynyloxybenzenesulfonyl)ethyl]benzyl}methanesulfonamide, or N-{4-[1-(formylhydroxyamino)-2-(4-oct-2-ynyloxybenzenesulfonyl)ethyl]benzyl}methanesulfonamide.

3. A medicament containing, as an active ingredient therein, a compound or a salt thereof or a solvate thereof as stated in claim 1.

4. The medicament according to claim 3, which is an ADAM17 inhibitor.

5. A method of treating rheumatoid arthritis, systemic lupus erythematosus, Crohn's disease, Behcet's disease, multiple sclerosis, Sjogren's syndrome, sepsis, asthma, atopic dermatitis, or psoriasis, or cancer, the method comprising administering to a subject in need of same an effective amount of the medicament of claim 3.

* * * * *